United States Patent
Hellenkamp

(10) Patent No.: US 6,605,099 B1
(45) Date of Patent: Aug. 12, 2003

(54) AUTOMATIC SURGICAL DEVICE AND CONTROL ASSEMBLY FOR CUTTING A CORNEA

(76) Inventor: Johann F. Hellenkamp, 10060 SW. 89th Ct., Miami, FL (US) 33176

( * ) Notice: Subject to any disclaimer, the term of this patent is extended or adjusted under 35 U.S.C. 154(b) by 0 days.

(21) Appl. No.: 09/690,204

(22) Filed: Oct. 17, 2000

Related U.S. Application Data

(63) Continuation of application No. 09/433,478, filed on Nov. 4, 1999, now Pat. No. 6,132,446, which is a continuation of application No. 09/065,848, filed on Apr. 24, 1998, now Pat. No. 6,007,553, which is a continuation-in-part of application No. 08/845,171, filed on Apr. 25, 1997, now Pat. No. 6,051,009, which is a continuation-in-part of application No. 08/598,180, filed on Feb. 7, 1996, now Pat. No. 5,624,456.

(51) Int. Cl.⁷ .............................................. A61B 17/32
(52) U.S. Cl. ........................................................ 606/166
(58) Field of Search .................................. 606/166, 167, 606/180, 4, 5, 172

(56) References Cited

U.S. PATENT DOCUMENTS

| | | |
|---|---|---|
| 2,457,772 A | 12/1948 | Brown et al. |
| 3,577,637 A | 5/1971 | Braginetz |
| 3,708,881 A | 1/1973 | Bennett |
| 3,879,847 A | 4/1975 | Roll |
| 4,173,980 A | 11/1979 | Curtin |
| 4,205,682 A | 6/1980 | Crock et al. |
| 4,429,696 A | 2/1984 | Hanna |
| 4,489,489 A | 12/1984 | Sarto |
| 4,517,741 A | 5/1985 | Castelluzzo |
| 4,642,892 A | 2/1987 | Ishida |
| 4,660,556 A | 4/1987 | Swinger et al. |
| 4,662,370 A | 5/1987 | Hoffmann et al. |
| 4,665,914 A | 5/1987 | Tanne |
| 4,674,503 A | 6/1987 | Peyman et al. |

(List continued on next page.)

FOREIGN PATENT DOCUMENTS

| | | |
|---|---|---|
| FR | 1366323 | 6/1964 |
| WO | WO 93/06783 | 4/1993 |
| WO | WO 95/31143 | 11/1995 |

OTHER PUBLICATIONS

1. Steinway Instrument Company, Inc., "The Steinway/Barraquer In–Situ Microkeratome Set" Brochure.

2. "New Methods in Refractive Corneal Surgery—An experimental Study," by J. Draeger et al., Klin. Mbl. Augenheilk, 192 (1988), pp. 458–461.

3. "A Semi–Automatic Electric Keratome for Lamellar Croneal Graft," by J. Draeger, Klin Mbl. Augenheilk, 167 (1975), pp. 353–359.

4. "Lamellar Refractive Keratoplasty," Bores Eye Institute, 1988, 1989, Chapter 4, pp. 1–9.

Primary Examiner—Michael J. Milano
Assistant Examiner—Vy Q. Bui
(74) Attorney, Agent, or Firm—Malloy & Malloy, P.A.

(57) ABSTRACT

A surgical device for cutting substantially across a cornea of an eye of a patient, the device including a positioning ring structured to be temporarily attached to a portion of the eye surrounding the cornea to be cut, and defining an aperture sized to receive and expose the cornea to be cut. The surgical device further includes a cutting head assembly structured to be guided and driven over an upper surface of the positioning ring in a generally arcuate path, and having a cutting element positioned therein and structured to oscillate laterally to facilitate smooth and effective cutting of the cornea. The cutting head assembly is structured to be detachably coupled to the positioning ring by a coupling member which permits movement of the cutting head assembly relative to the positioning ring along the generally arcuate path, but maintains sufficient engagement therebetween to ensure that smooth, steady, driven movement is maintained.

9 Claims, 9 Drawing Sheets

U.S. PATENT DOCUMENTS

| | | |
|---|---|---|
| 4,688,570 A | 8/1987 | Kramer et al. |
| 4,744,144 A | 5/1988 | Lowery, Sr. et al. |
| 4,807,623 A | 2/1989 | Lieberman |
| 4,813,132 A | 3/1989 | Castelluzzo |
| 4,884,570 A | 12/1989 | Krumeich et al. |
| 4,903,695 A | 2/1990 | Warner et al. |
| 4,943,296 A | 7/1990 | Funakubo et al. |
| 4,997,437 A | 3/1991 | Grieshaber |
| 5,108,412 A | 4/1992 | Krumeich et al. |
| 5,133,726 A | 7/1992 | Ruiz et al. |
| 5,215,104 A | 6/1993 | Steinert |
| 5,288,292 A | 2/1994 | Giraud et al. |
| 5,318,044 A | 6/1994 | Kilmer et al. |
| 5,337,482 A | 8/1994 | Schmidt |
| 5,342,378 A | 8/1994 | Giraud et al. |
| 5,368,604 A | 11/1994 | Kilmer et al. |
| 5,395,385 A | 3/1995 | Kilmer et al. |
| 5,403,335 A | 4/1995 | Loomas et al. |
| 5,464,417 A | 11/1995 | Eick |
| 5,486,188 A | 1/1996 | Smith |
| 5,586,980 A | 12/1996 | Kremer et al. |
| RE35,421 E | 1/1997 | Ruiz et al. |
| 6,007,553 A * | 12/1999 | Hellenkamp et al. ....... 606/166 |
| 6,132,446 A * | 10/2000 | Hellenkamp et al. ....... 606/166 |

* cited by examiner

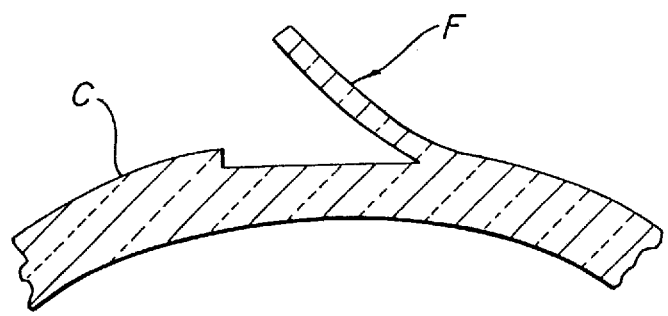
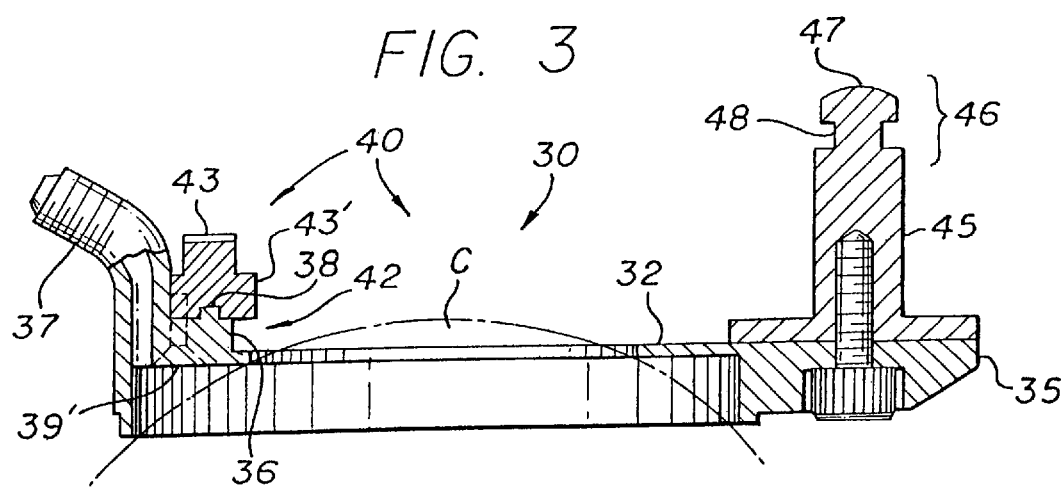
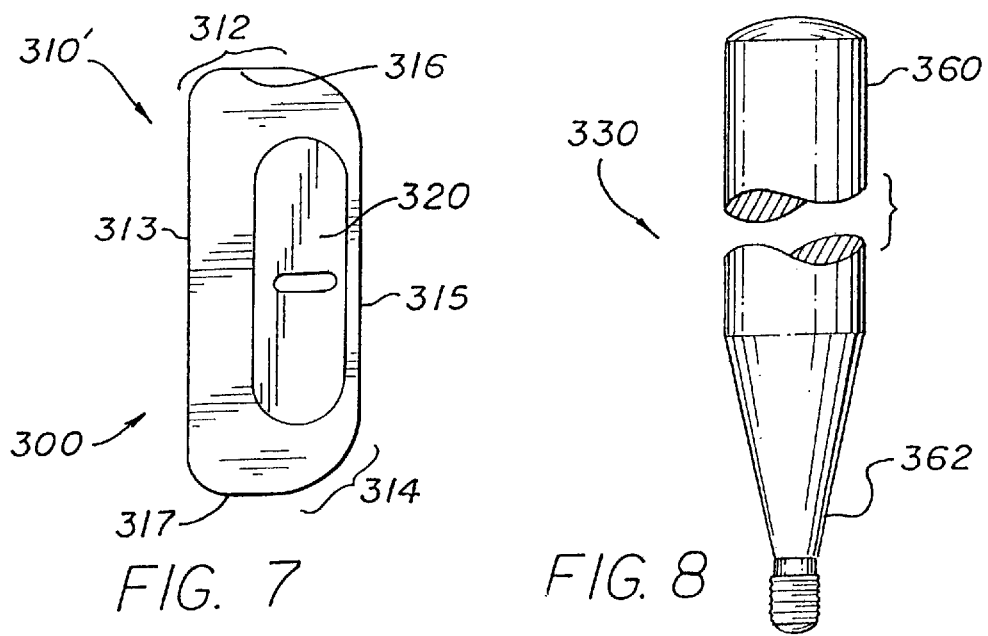

FIG. 5-A
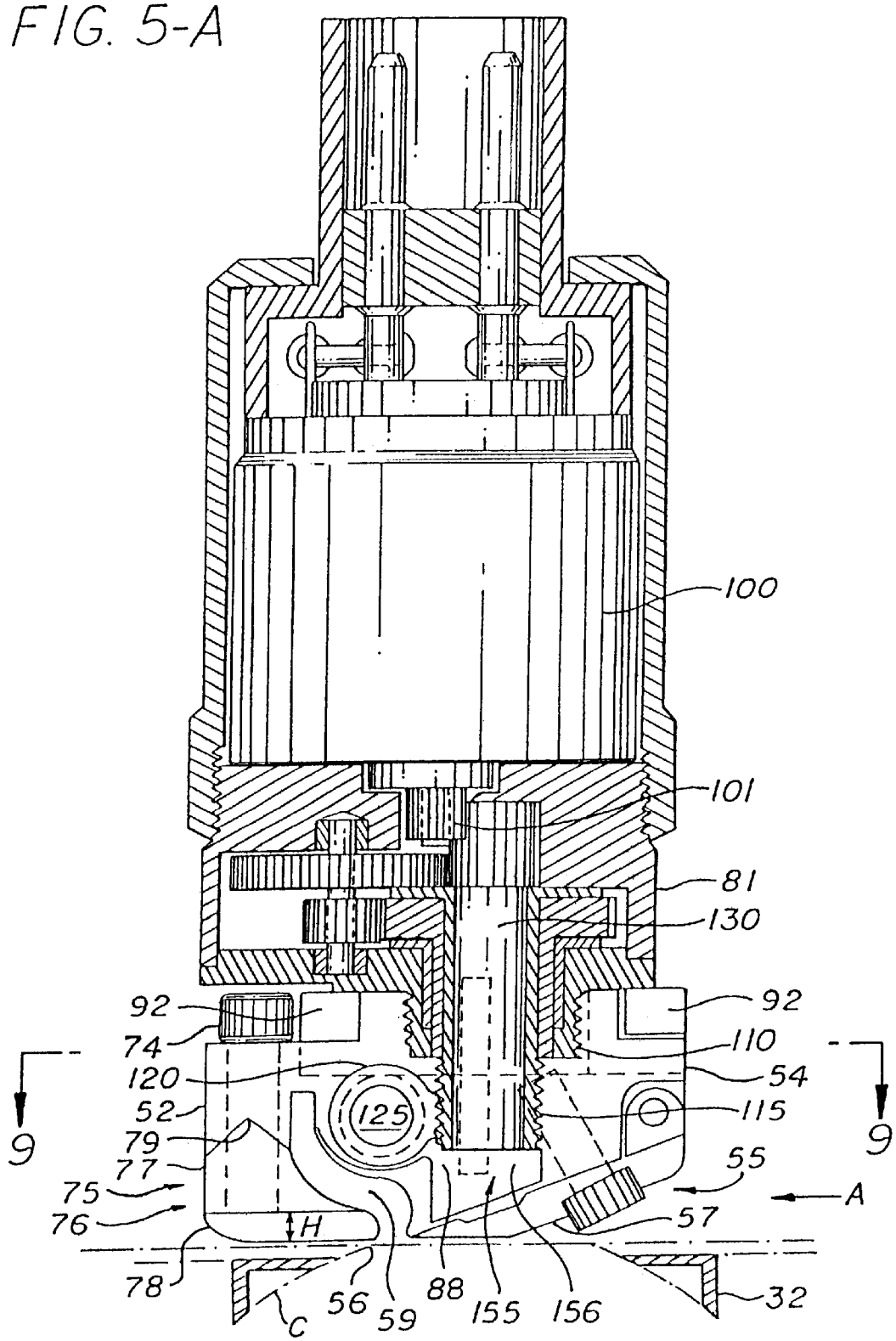

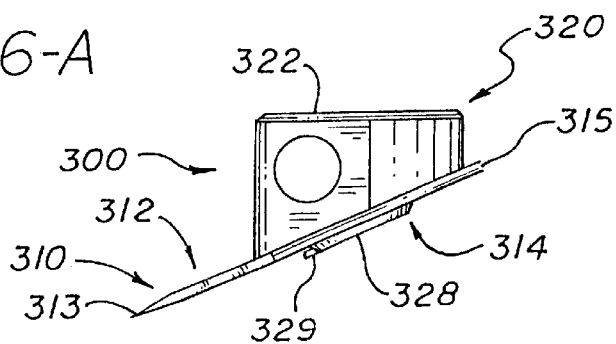
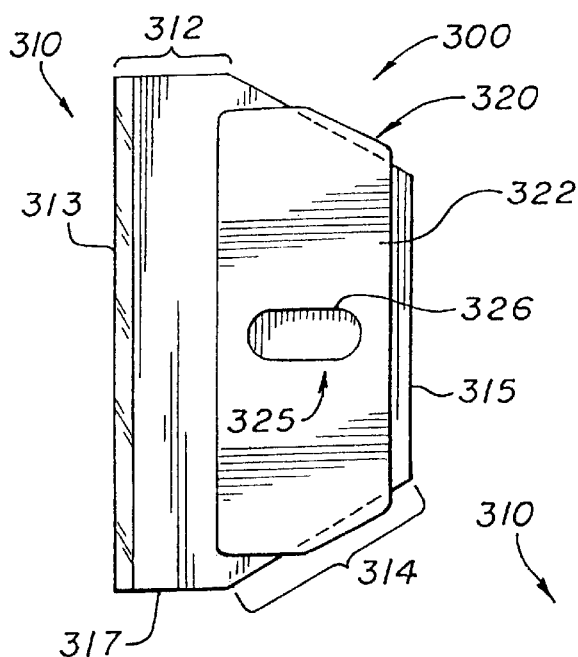
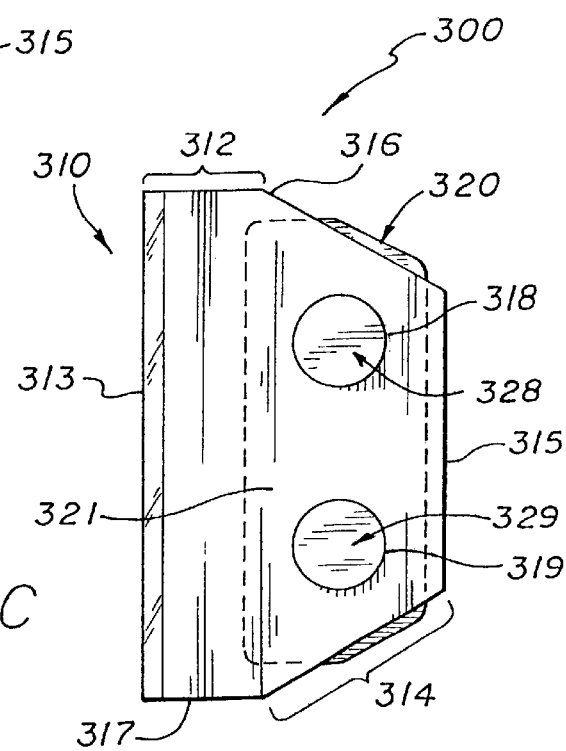

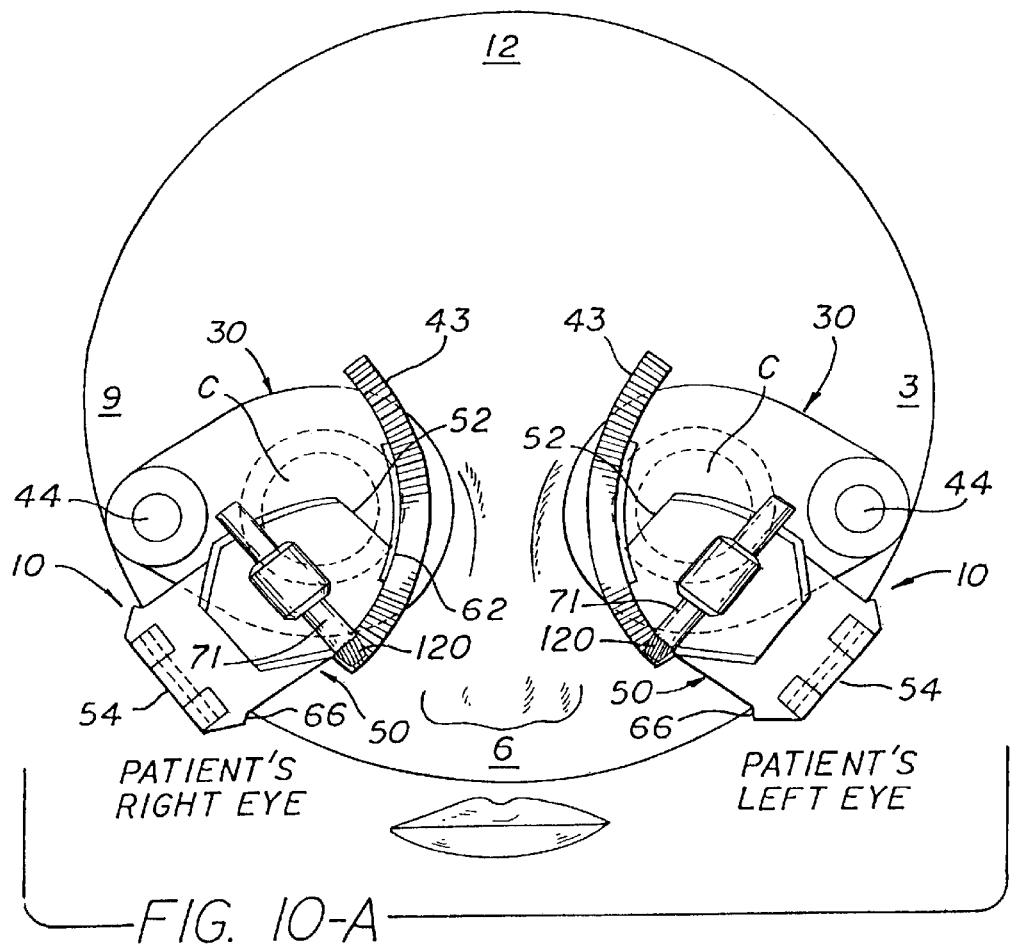
FIG. 10-A
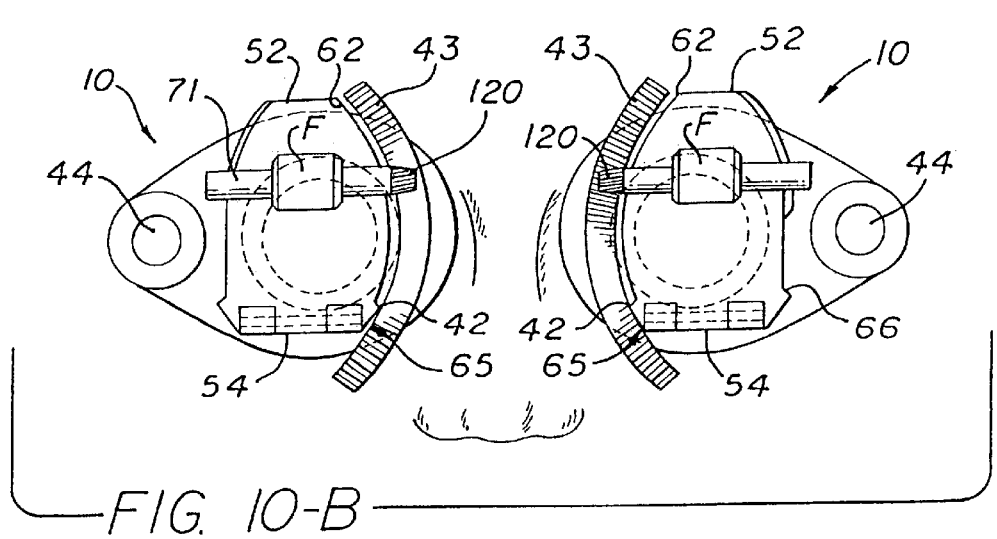
FIG. 10-B

AUTOMATIC SURGICAL DEVICE AND CONTROL ASSEMBLY FOR CUTTING A CORNEA

CLAIM OF PRIORITY

The present application is a continuation to an earlier filed, U.S. patent application having Ser. No. 09/433,478 which was filed on Nov. 4, 1999 and which is set to mature into U.S. Pat. No. 6,132,446 on Oct. 17, 2000, which is a continuation to patent application having Ser. No. 09/065, 848 which was filed on Apr. 24, 1998, which matured into U.S. Pat. No. 6,007,553; which is a Continuation-In-Part to an earlier filed, U.S. patent application having Ser. No. 08/845,171 filed Apr. 25, 1997, which matured into U.S. Pat. No. 6,051,009, incorporated herein by reference, which is a Continuation-in-Part of U.S. Patent Application having Ser. No. 08/598,180 filed Feb. 7, 1996, also incorporated herein by reference, which matured into U.S. Pat. No. 5,624,456 on Apr. 29, 1997.

BACKGROUND OF THE INVENTION

1. Field of the Invention

The present invention relates to an improvement in a medical apparatus used during the performance of eye surgery. In particular, the present invention is directed towards an improved cutting blade assembly to be used in conjunction with an automatic surgical device for cutting the cornea of a patient's eye. The present invention is further directed towards a control assembly for use with an automatic surgical device which is capable of shutting off power supplied to the device when problems are encountered during the surgical cutting of the cornea.

2. Description of the Related Art

Until about twenty years ago, refractive errors of light passing through the eye could only be treated with eyeglasses or contact lens, both of which have well known disadvantages for the user. Consequently, in the last several years, research has been directed to surgical operations to change the refractive condition of the eye, i.e., either to flatten or increase the curvature of a patient's eye depending upon his or her condition. The desired result of such surgical operations is that light rays passing through the cornea will be refracted to converge properly and directly onto the retina so as to allow a patient to clearly see close or distant images.

Automated Lamellar Keratectomy (ALK) is one surgical technique developed wherein the eye is first numbed by a drop of anesthetic, and then a suction ring is placed on the eye to carefully position the cornea (termed "centration" in the art) for being cut by a very fine microsurgical instrument known as a microkeratome. The microkeratome is generally a blade carrying device that must be manually pushed or mechanically driven in a cutting path across the suction ring simultaneous with the motorized movement of the cutting element, which movement is transverse to the direction of the cutting path. For treating myopia pursuant to ALK procedures, the microkeratome is typically used to first cut into the cornea so as to raise and separate a thin layer of the anterior cornea of between 100–200 microns in depth and about 7 millimeters in diameter. Next, the microkeratome is then used to make a second pass over the cornea to resect or remove a smaller part of the cornea, generally about 4 to 6 millimeters in diameter, which is then discarded. The anterior corneal cap which was cut away with the first pass of the microkeratome is then put back into its original position, without suturing, for healing to occur. The desired result of this procedure is that the cornea will have a new curvature because of the resected tissue, which provides a new refracting surface to correct the patient's original myopic condition. To correct hyperopia under ALK however, the microkeratome is typically used to make a single deep pass over the cornea. The cut layers are put back into their original position, without any removal of any other tissue. Because of the depth of the cut, the intraocular pressure within the eye causes a steepening of the cornea to again, provide a new refracting surface which hopefully will correct the patient's original hyperopic condition.

Another more recent advance in surgical procedures to correct refractive errors of the eye involves the introduction of laser procedures. One such procedure, known as Laser Intrastromal Keratomileusis, (LASIK), is currently considered optimal because it allows sculpting of the cornea by a laser, without damaging adjacent tissues. Moreover, with the aid of computers, the laser can be programmed by a surgeon to precisely control the amount of tissue removed, and significantly, to permit more options for the reshaping of the cornea. Under LASIK procedures, the eye is still typically positioned within a suction ring and a microkeratome is typically used to cut into the cornea so as to raise a thin layer of the cornea.

In recent years, it has been learned that regardless of whether ALK or LASIK surgery is performed, the microkeratome which cuts the cornea should not create a corneal cap nor separate the cut corneal tissues completely from the rest of the cornea. The reasons are primarily two-fold: first, the possibility exists that when the corneal cap is put back in place on the cornea, it will not be aligned properly with the remaining corneal tissues, which has several drawbacks for the patient, and second, the possibility exists that the corneal cap will become lost during the surgery, and if that occurs, the consequences for the patient are catastrophic. In great part to overcome these problems, among others, the inventor of the invention described in the present application created and developed an improved surgical device for cutting the cornea which automatically and reliably leaves a portion of the raised and separated corneal tissues connected or "hinged" to the eye, thereby forming a raised layer of corneal tissue hinged to the eye, known as a corneal flap F, illustrated in FIG. 1.

Significantly, it has been determined that the corneal flap should have a depth of no less than 130 microns and no more than 160 microns to yield optimal results. It should be borne in mind that achieving this result during surgery requires an extremely precise instrument as one micron is a unit of length equal to one thousandth of a millimeter. Further, it is desirable, if not imperative, for the microkeratome to cut across the cornea in a manner that will very finely and smoothly cut the corneal tissues. In this regard, there is a need in the art for improvement in that when the smoothness of a cut made to the cornea by known microkeratome devices is closely examined under a microscope, the cut, corneal tissue edges are seen to be a bit irregular, if not slightly jagged. It would be ideal if a microkeratome device were able to cut across the cornea, not only so as to cut and raise the microscopicly thin layer of corneal tissue currently considered optimal, but to do so in a manner which results in a noticeably improved cut to the cornea, namely, by yielding very fine, smooth and almost undetectable cut corneal tissue edges.

In addition, there is room for known microkeratome devices to be improved with regard to the assembly required prior to performing surgery on a patient's eye, as well as with regard to the disassembly, sterilization and cleaning of the device, or parts thereof, following surgery. Specifically, microkeratome devices, and particularly, the cutting blade housed therein, which penetrates into and cuts the cornea must be in a proper sanitary and sterilized state until generally about the moment when surgery on the eye is to begin. Known microkeratome devices, however, have required that the housing for the cutting blade be manipulated so as to create access to an interior thereof and permit the placement of the cutting blade therein, which itself must typically be handled as well, after which, the housing must again be manipulated so as to close off the access means, all of which has hopefully resulted in the cutting blade being properly in place. This excessive manipulation required of known microkeratome devices is not conducive, however, to maintaining the proper sanitary and sterilized state required for surgery. Moreover, in manipulating the access means of certain known microkeratome devices, some surgeons have unintentionally caused the cutting blade to become dislodged, or worse, have even bent the cutting blade, thereby requiring the assembly process to start over again. Further, the mechanisms within known microkeratome devices for holding the cutting blade have been designed for repeated use. This factor tends to only exacerbate the problems encountered in the art in that these known blade holding mechanisms should also be removed from the microkeratome device following a surgery in order to be properly cleaned and/or sterilized for subsequent use. The assembly and disassembly of these mechanisms are not only tedious and time consuming, but are fraught with the difficulties of maintaining sterilization and ensuring proper re-assembly.

Consequently, there is a need in the art for an improved microkeratome device for cutting the cornea of a patient's eye which can easily receive and which facilitates the proper positioning of a cutting blade therein, without excessive manipulation. There is also a need for an improved cutting blade assembly that facilitates easy insertion within a microkeratome device, with little danger of becoming bent, while simultaneously offering the user the knowledge that it is securely and properly in place. Any such improved cutting blade assembly should similarly be quickly and easily removed from the microkeratome device, and will preferably be disposable. It would be ideal if any such improved cutting blade assembly could be readily packaged in containers that permit sterilization prior to shipping, and which remain sterilized during shipping, and further, which could be easily removed from the sterile packaging for insertion into the microkeratome while maintaining sterility. In this regard, any such improved cutting blade assembly would ideally include an instrument which facilitates the removal of the assembly from a sterile container and the insertion thereof into the microkeratome, while maintaining sterility.

Known microkeratome devices are thought to have other, fairly significant deficiencies as well. For example, when a surgery on a patient's eye is underway, at times the suction or vacuum provided to temporarily attach the positioning ring to the cornea is either broken or interrupted. Given the precision cutting which is needed for such surgeries, however, it is highly undesirable, for the eye to continue to be cut during such situations. To date, known microkeratome devices continue cutting in such situations. Thus, it would be highly beneficial to provide an improved microkeratome device with a control assembly that could detect problems encountered during the surgical cutting of the cornea and that will shut off power supplied to the device when problems are detected so as to stop the cutting of the cornea by the microkeratome. Moreover, if surgery on a patient's eye is proceeding well, but there is sudden power loss, any such control assembly should enable the microkeratome device to continue functioning during the rather short duration of the operation, without interruption, both in terms of continuing to ensure a power supply to the device and a supply of vacuum to the positioning ring.

SUMMARY OF THE INVENTION

The present invention is designed to satisfy the needs which remain in the art of microkeratome devices used to cut the cornea of a patient's eye. In this regard, the present invention is directed towards an improved microkeratome which is able to cut and raise a microscopicly thin layer of corneal tissue in a manner that results in very fine, smooth and almost undetectable cut corneal tissue edges. In addition, the present invention is directed towards an improved microkeratome cutting blade assembly that permits quick and easy installation and removal from the microkeratome housing, without excessive manipulation. The present invention is further directed towards a control assembly for a microkeratome device that is capable of detecting problems encountered during the surgical cutting of the cornea and either shutting off power supplied to the device, if appropriate, or ensuring that power and/or a vacuum continue to be supplied to the device, if appropriate.

The cutting blade assembly of the present invention is seen to comprise an improved cutting blade and blade holder. The cutting blade comprises a front portion that includes a sharp, forward cutting edge, a rear, trailing portion having a rear edge, and a pair of side edges that extend and taper between the front and rear trailing portions. The cutting blade further includes at least one aperture formed therein, and preferably, a pair of apertures disposed in the rear, trailing portion in substantially aligned relation with one another. Preferably, the cutting blade is substantially flat and made of stainless steel, with the front portion of the cutting blade having an overall dimension which is larger than the rear trailing portion. The blade holder of the improved cutting blade assembly is formed so that an underside thereof is secured to the cutting blade at the at least one aperture on the cutting blade, and so that a top side of the blade holder includes means for being operably driven by the drive means of the microkeratome device, which may comprise a recess formed within the blade holder. In the preferred embodiment, the blade holder will be molded of a plastic material and will be press fit during manufacture into the at least one aperture on the cutting blade so as to provide an integrally formed cutting blade assembly. In a most preferred embodiment, the cutting blade assembly of the present invention will additionally comprise a tool which facilitates the removal of the cutting blade and blade holder from a sterile packing container and the insertion thereof in a microkeratome device, while maintaining sterility.

A primary object of the present invention is to provide an improved microkeratome and cutting blade assembly that markedly improves the cutting of the cornea, namely, one that is able to cut and raise a microscopicly thin layer of corneal tissue in a manner that results in very fine, smooth and almost undetectable cut corneal tissue edges, which can then be easily and more precisely aligned back into an original position on the cornea following the reshaping of the cornea.

Another primary object of the present invention is to provide a microkeratome device with improved access means for ensuring that either or both a cutting blade and blade holder can be easily and quickly installed for surgical use on a patient, while at the same time, facilitating cleaning of the microkeratome and one or more of its internal mechanisms.

It is a further important object of the present invention to provide a cutting blade assembly which is easily and quickly installed within a microkeratome device in preparation for surgical use on a patient, without excessive handling so as to maintain the sanitary condition of the assembly and device, and further which quickly offers confirmation that the assembly is securely and properly in place within the microkeratome.

It is also an object of the present invention is to provide an improved cutting blade and blade holder which is integrally formed and consequently, which is easy to remove from a microkeratome device, and ideally, which is disposable.

Yet another object of the present invention is to provide a cutting blade assembly which is readily packaged in containers that permit sterilization prior to and which remain sterilized during shipping, and further, which is easily removed from the sterile packaging for insertion into the microkeratome while simultaneously maintaining sterility.

A further object of the present invention is to provide a cutting blade assembly which can be used with either presently known microkeratome devices or with those that may be developed in the future.

It is a further object of the present invention to provide an improved automated microkeratome device which is not only readily usable on either a patient's left or right eye, but which readily informs a surgeon as to which eye the device is assembled for use on.

Yet another important object of the present invention is to provide an improved microkeratome device having a control assembly which will not allow the cutting of the cornea to continue during a surgery when the vacuum seal between the positioning ring and the eye becomes compromised and/or is broken.

Still another important object of the present invention is to provide a control assembly for a microkeratome device that is capable of detecting problems encountered during the surgical cutting of the cornea and which has back up capabilities to ensure that power and/or a vacuum continue to be supplied to the device.

A feature of the present invention is that it provides a control assembly for a microkeratome device that is internally electrically isolated between the high voltage and low voltage sides, while still permitting necessary checks and interaction between the components on both sides.

Another feature of the present invention is that it provides a control assembly for a microkeratome device that will not permit a motor to burn out if substantial resistance is encountered by the device as it cuts the cornea during an operation.

These and other objects, features and advantages of the present invention will be more readily understood upon consideration of the accompanying drawings as well as the detailed description of a preferred embodiment for the invention, which is set forth below.

BRIEF DESCRIPTION OF THE DRAWINGS

For a fuller understanding of the nature of the present invention, reference should be had to the following detailed description taken in connection with the accompanying drawings in which:

FIG. 1 is schematic illustration of a cornea of an eye wherein a corneal flap has been created.

FIG. 3 is a cross sectional view of the retaining and positioning means shown in FIG. 2.

FIG. 5-A is a partial cross sectional view of the preferred microkeratome in a partially disassembled state so as to illustrate the improved access means, without a cutting blade assembly inserted therein.

FIG. 6-A is a side view of the cutting blade assembly according to the present invention in a preferred embodiment.

FIG. 6-B is a top plan view of the cutting blade assembly illustrated in FIG. 6-A.

FIG. 6-C is a bottom view of the cutting blade assembly illustrated in FIG. 6-A.

FIG. 7 is a top plan view of the cutting blade assembly of the present invention in an alternative embodiment.

FIG. 8 is a side view of a tool which facilitates the removal of the cutting blade assembly shown in FIGS. 6 and 7 from a sterile packing container and the insertion thereof in a microkeratome device, while maintaining sterility.

FIG. 10-A is a front schematic illustration of the preferred microkeratome in use on both a patient's left and right eyes and illustrating the cutting head assembly in the initial position.

FIG. 10-B is a front schematic illustration of the preferred microkeratome illustrated in FIG. 10-A but depicting the cutting head assembly in the movement stopped position wherein a corneal flap has been formed with the resulting hinged portion being oriented so as to cooperate with the blinking of the eye following surgery.

Like reference numerals refer to like parts throughout the several views of the drawings.

DETAILED DESCRIPTION OF THE PREFERRED EMBODIMENT

Figure 2:
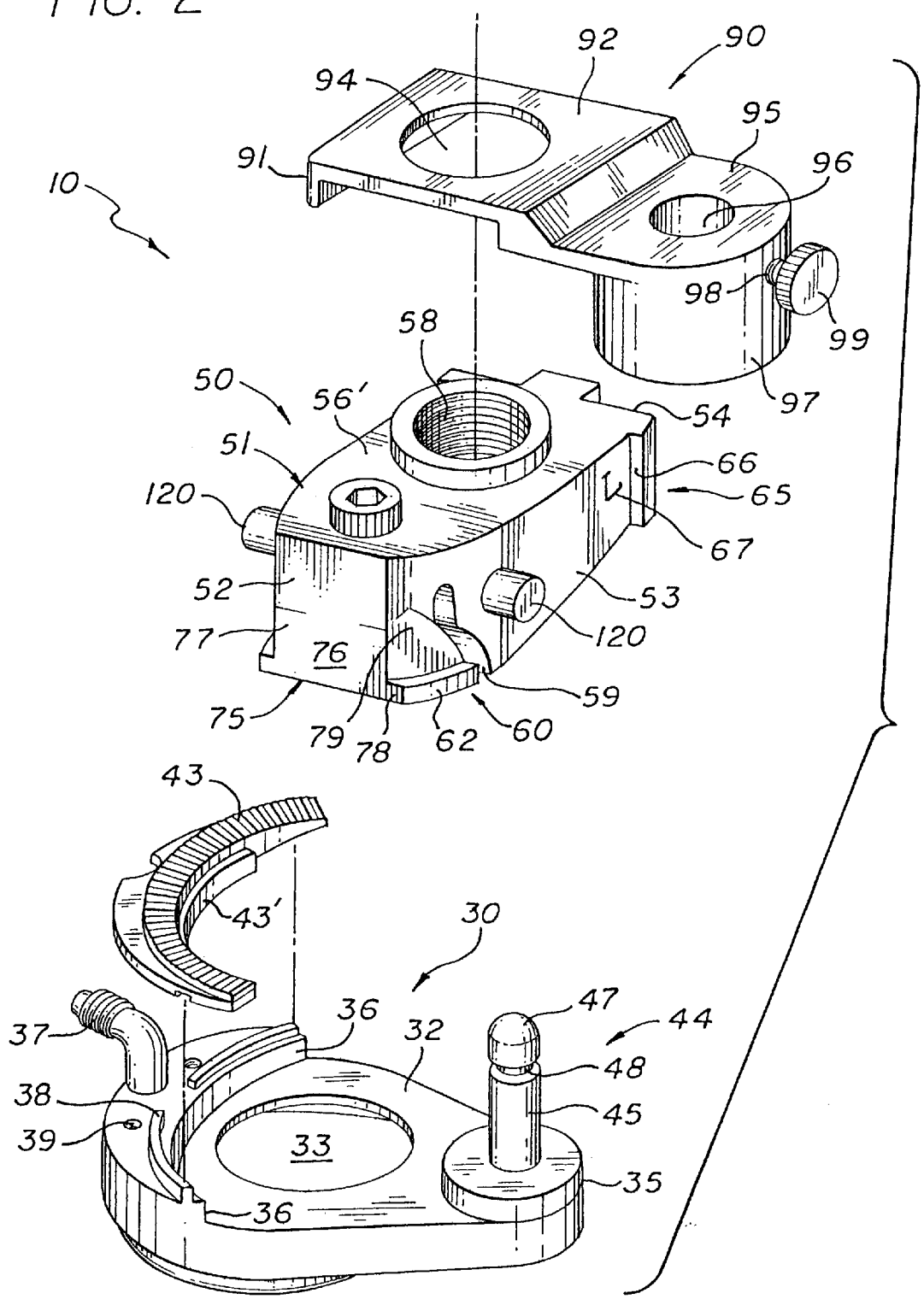
FIG. 2 is an exploded perspective view of a preferred microkeratome retaining and positioning means, of a preferred microkeratome cutting head assembly, as well as a preferred microkeratome coupling member according to the present invention.

As illustrated throughout the Figures, the present invention is directed towards an improved automatic microkeratome device for smoothly cutting the cornea of an eye, generally indicated by reference numeral 10, and towards a cutting blade assembly therefor, generally indicated by reference numeral 105, and towards a control assembly therefor, generally indicated by reference numeral 200.

The preferred and improved automatic microkeratome device of the present invention, which is structured to cut substantially but not completely across the cornea of a patient's eye so as to raise a thin layer thereof and create a hinged flap of corneal tissue, will be discussed first. As illustrated in FIGS. 2 and 3, the preferred microkeratome device 10 includes means 30 for retaining and positioning the eye on which surgery is to be performed. The retaining and positioning means 30, which may be made of high grade stainless steel, preferably comprise a positioning ring 32 having an aperture 33 formed therein. The aperture 33 is sized to permit the cornea C, of the eye to pass therethrough and be exposed, as depicted in FIG. 3. As illustrated, the positioning ring 32 is preferably defined by a generally tear-drop shape.

Figure 11:
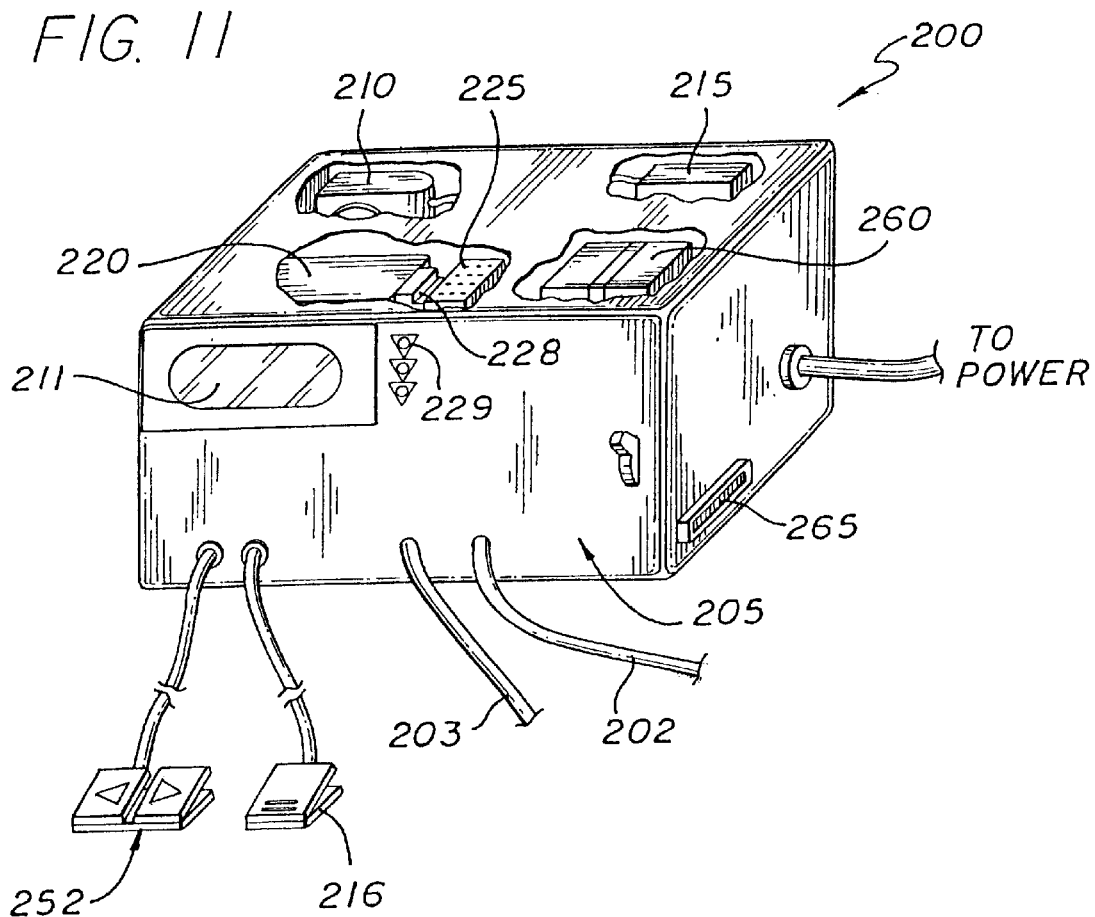
FIG. 11 is a perspective, partial cut away view of a preferred control assembly configuration according to the present invention which is to be used with a microkeratome device such as illustrated in FIG. 2.
Figure 12:
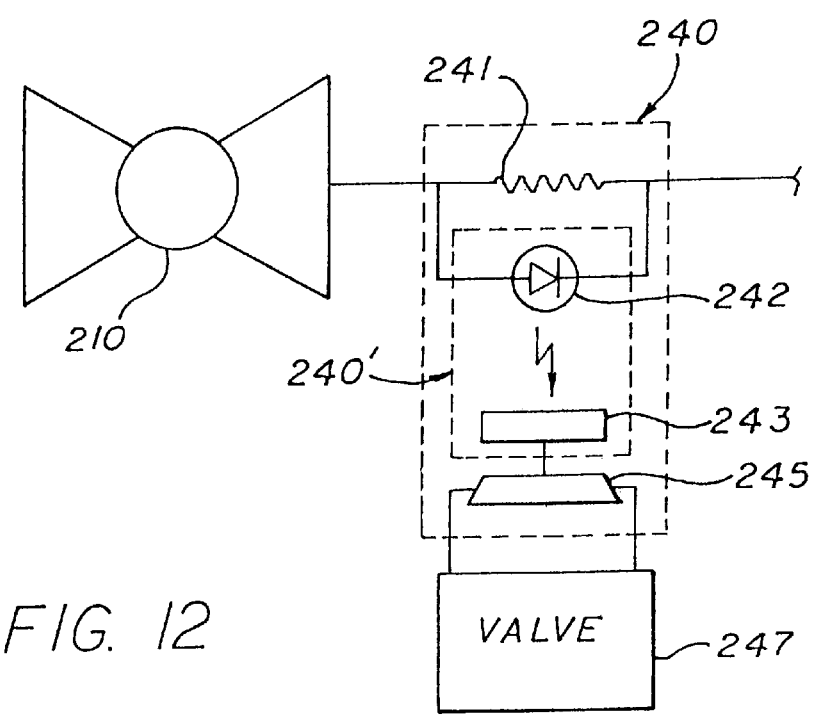
FIG. 12 is an isolated diagram of the configuration of a preferred optic coupler for the control assembly according to the present invention.

Positioning ring 32 further includes means for being temporarily attached to a portion of the eye surrounding the cornea on which surgery is to be performed. Ideally, the temporary means include suctioning means. For example, positioning ring 32 preferably includes a connection member 37, which as illustrated in FIG. 2 and 3, is in fluid communication with an undersurface of positioning ring 32. Connection member 37 is adapted to be interconnected with a vacuum hose 202, which as shown in FIG. 11, may be connected to a vacuum pump 210, such that when suction occurs, the undersurface of positioning ring 32 forms a seal about and is retained about the corneal portion of the eye which is about to undergo surgery. Further, the structure of positioning ring 32, accompanied by the suctioning, acts to properly position the cornea C, for surgery and to maintain the position during surgery as well. Typically, a vacuum of about 25 inches of Hg at sea level will be used.

The retaining and positioning means 30 further include guide means 40 formed thereon, best illustrated in FIG. 3. Guide means 40 may be formed directly on the positioning ring 32, so as to be integral therewith, or may be operably connected thereto as a separate element. In any event however, the guide means 40 will be disposed on positioning ring 32 so as to guide and facilitate movement of the cutting head assembly 50, discussed below, during the surgical cutting of the cornea. Referring to FIG. 3, in the preferred embodiment, guide means 40 are seen to comprise a channel member 42, which extends along a length of at least one side of positioning ring 32 and preferably, on an upper surface of positioning ring 32. It will also be appreciated from the drawings that channel member 42 extends across ring 32 in an arcuate or semi-circular path. In the most preferred embodiment channel member 42 is formed by the interconnection of two separate elements, namely, an upwardly and arcuately extending sidewall 36 formed on positioning ring 32, and a toothed track 43 which is interconnected with sidewall 36. Still referring to FIG. 3, in the most preferred embodiment, positioning ring 32 is seen to include the upwardly and arcuately extending sidewall 36 having a ridge 38 formed on an upper surface thereof, and extending partially if not completely along, at least one side of positioning ring 32. Further, in this preferred embodiment, the toothed track 43 is structured to be operably connected to ridge 38 by way of mating structure. For example, the mating structure can be in the form of a receiving groove disposed on the undersurface of toothed track 43, and/or by way of conventionally known fasteners 391 such as screws, rivets, etc. which may pass through positioning ring 32 at apertures 39 and extend into toothed track 43. As further illustrated in FIG. 3, toothed track 43 is seen to include a lip 43' which is sized and dimensioned to protrude beyond the vertical plane formed by sidewall 36. Thus, guide means 40 in the form of a generally "C" shaped channel member 42 is comprised by the combined structure of sidewall 36 and toothed track 43, having lip 43'. It will be appreciated that toothed track 43 cooperates with the drive means 80 (see FIGS. 4 and 9) so as to drive the cutting head assembly 50 across positioning ring 32, as more fully discussed below, and may be on an interior or the preferred exterior of the drive means 80.

The guide means 40 further comprise a rigid upstanding member 44 disposed on the retaining and positioning means 30, and generally opposite the toothed track 43. As will again be appreciated from the drawings, in the preferred embodiment, wherein positioning ring 32 is of a tear-drop shape, rigid upstanding member 44 comprises a post member 45 securely connected to positioning ring 32 on an upper surface thereof at or near a tip 35 thereof. From the explanation which follows, it will become clear that channel member 42 and rigid upstanding member 44 permit the cutting head assembly 50 of this invention to become effectively guided and securely received on the positioning ring 32 in two places while still permitting cutting head assembly 50 to be smoothly and slidably moved over positioning ring 32 along a generally arcuate path, by way of a pivoting motion about rigid upstanding member 44.

Referring now to FIG. 2, the preferred microkeratome device is seen to include a cutting head assembly 50. A primary purpose of the cutting head assembly 50 is to house a cutting element 70 such as a cutting blade, see FIG. 5, with a cutting surface operatively exposed therefrom. As such, upon the cutting head assembly 50, with the cutting element 70 operatively disposed therein, being moved across the cornea retained within positioning ring 32, the cornea may be precisely cut by cutting element 70. To accomplish this, cutting head assembly 50 includes a main housing 51 containing the cutting element 70. Additionally, included in the main housing 51 is an aperture 58 structured and disposed to permit drive means 80 to be operably connected thereto (see FIGS. 4 and 9) and to thereby drive the cutting head assembly 50 across positioning ring 32 in order to effectively cut the cornea. Further, as the cutting head assembly 50 must be driven in a smooth and controlled manner across the cornea, housing 51 includes tracking means 60 which are structured and disposed for mating communication with and tracking within channel member 42, of positioning ring 32, in order to precisely guide the cutting head assembly 50, and therefore the cutting element 70, along the defined arcuate path. Finally, as a significant feature of the preferred microkeratome device is to cut a portion of the cornea without completely severing it, abutting or stop means 65 are provided, which serve the purpose of limiting and preferably, completely stopping the movement of the cutting head assembly 50 from cutting completely across the cornea, that is, before the assembly has passed completely over the cornea. The abutting or stop means are preferably disposed on the main housing 51. These features will be discussed in more detail below.

Still referring to FIG. 2, the preferred microkeratome device is also seen to include a coupling member 90. Coupling member 90 is structured and disposed to movably couple the cutting head assembly 50 to the positioning ring 32 while simultaneously permitting movement of the cutting head assembly 50 relative to positioning ring 32. As illustrated in FIG. 2, coupling member 90 comprises two segments: a) a retaining segment 92 and b) a pivot segment 95. The retaining segment 92 is structured and disposed to be fitted onto a top wall surface 56' of main housing 51 and may include downwardly depending flanges 91, 93 to snugly receive and grip a portion of housing 51 therebetween. The retaining segment 92 also includes an aperture 94 formed therein to correspond to aperture 58 of housing 51. As such, aperture 94 is sized and configured to allow passage of the driving shaft of the driving means 80 (shown in FIGS. 4 and 9) therethrough and into aperture 58 of the housing 51. Thus, in assembled form, coupling member 90 is securely yet removably coupled to head assembly 50 as a result of the engagement of the driving means 80 with the housing 51 through retaining segment 92. Turning to the pivot segment 95 of coupling member 90, it is structured and disposed to be coupled to rigid upstanding member 44 of positioning ring 32 and to permit coupling member 90, and accordingly, the cutting head assembly 50 connected thereto, to pivotally move about post member 45. Preferably, pivot segment 95 includes a bushing 97 having a bore 96 formed therein, which is sized to receive a substantial height of post member 45, thereby captivating it therein. Further, the pivot segment 95 preferably includes maintaining means 46, see FIG. 3, for maintaining rigid upstanding member 44 within bushing 97 and engagement means 98 for maintaining bushing 97 over rigid upstanding member 44. As illustrated in FIGS. 2 and 3, the maintaining means 46 preferably include an enlarged head 47 on rigid upstanding member 44, and an annular recess 48 or taper about the neck section of upstanding member 44. As illustrated, the engagement means 98 preferably comprise a threaded shaft which passes through a sidewall of bushing 97 and can be selectively moved into engagement with upstanding member 44 by rotating handle 99 and causing a tip thereof to extend into the annular recess 48, thereby preventing removal of the pivot segment 95 from the upstanding member 44, when surgery is to take place. It will therefore be appreciated that in assembled form, the engagement means 98 and maintaining means 46 cooperate to permit coupling member 90 and cutting head assembly 50 to rotate about upstanding member 44 while preventing bushing 97 from sliding up and off of upstanding member 44. It will also be appreciated that in assembled form, upstanding member 44 acts as additional guide means for enabling the cutting head assembly 50 to be driven along an arcuate path in a smooth and controlled manner across positioning ring 32 and thus, the cornea C.

With reference to FIG. 2, the cutting head assembly 50 of the preferred microkeratome device as well as its operation will now be described in more detail. As previously recited, the cutting head assembly 50 comprises the main housing 51 which includes a top surface 56', a bottom wall, and a surrounding sidewall structure 53 defining a front end face 52, and an oppositely disposed rear end face 54. Because during surgery, the cutting head assembly 50 is driven across positioning ring 32 along an arcuate path, front end face 52 preferably defines a tapered nose to cooperate with the arcuate path of channel member 42. Also as previously recited, the main housing is structured to contain the cutting element 70, such as a cutting blade, and to operatively expose a cutting surface thereof. In order to accomplish this, the main housing 51 is preferably structured to define an interior chamber 88, therein, see FIG. 5, which is structured to receive in a cutting position and to accommodate the operation of the cutting element 70 during surgery, and preferably, of a blade cutting assembly 300, described more fully below. A cutting opening 56 is formed at a bottom of housing 51 so as to expose a cutting surface of cutting element 70, as is best illustrated in FIG. 5.

Additionally, in order to permit a used cutting element 70 to be removed and replaced, housing 51 includes access means 55. In one embodiment, and as seen in FIG. 5, access means 55 at least partially form bottom wall of housing 51 near rear end face 54, and ideally, comprise a door member 57 which is hingedly connected to the surrounding sidewall structure 53 at rear end face 54. Door member 57 is movable between a closed operative position for surgery and an open position for permitting a used or contaminated cutting element 70 to be removed from the housing 51 and replaced with a new or sterile cutting element. Door member 57 may be selectively maintained in the closed position by conventionally known fasteners as depicted in FIG. 5. It should be noted that the door member 57 does not completely bridge the cutting element 70, which is thought to offer a sturdier and less fragile structure so as to avoid bending the cutting element when it is inserted and closed into position for use within the microkeratome.

Figure 5:
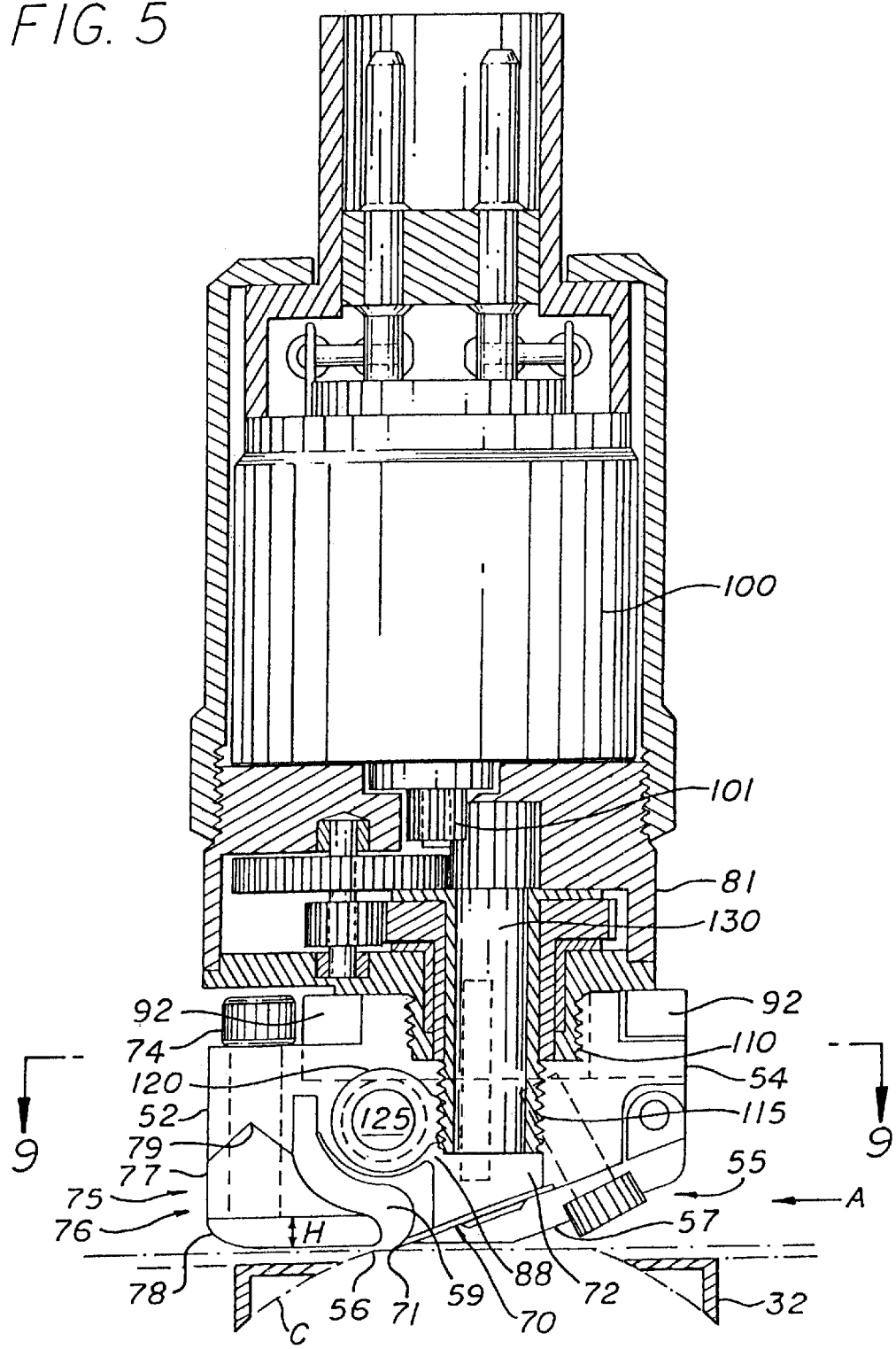
FIG. 5 is a partial cross sectional view of the preferred microkeratome illustrated in FIG. 4.

A unique feature of the present invention, however, is to provide the cutting head assembly 50 of the microkeratome device with improved access means, see FIG. 5-A, indicated generally by reference numeral 155, such that in preparation for surgery, a fresh and sterilized cutting element can be easily and quickly inserted within the cutting head assembly 50, with minimal handling so as to maintain it in a sanitary condition. Preferably, the improved access means 155 permit a fresh cutting element 70, and ideally, a cutting blade assembly 300 which includes both a cutting blade and a blade holder, described below, to be slidably inserted into the cutting head assembly, 50 and to be easily and yet properly secured in place therein in order for surgery to take place. To accomplish this, the improved access means 155 preferably comprise a side entry, access opening formed in the cutting head assembly 50. As illustrated in FIG. 5-A, more preferably, the surrounding sidewall structure 53 of the cutting head assembly 50 is structured to include an access opening 156 formed therein which further, is disposed to generally correspond and align with the location of interior chamber 88 of the cutting head assembly 50, so that the cutting element 70 may be received in a proper cutting position within the cutting head assembly 50 for surgery to take place. Ideally, the access opening 156 is structured and disposed to extend completely through the cutting head assembly 50 from one side of the surrounding sidewall structure 53 to the other, so that the cutting element 70 can be easily inserted from either side of the cutting head assembly 50. It should be appreciated from the foregoing that the improved access means 155 are additionally structured and disposed to permit easy and quick removal of a used and contaminated cutting element 70 from the cutting head assembly. It should further be appreciated that while the door member 57 of the cutting head assembly 50 can also be moved to an open position so as to permit insertion of a cutting element 70 within the cutting head assembly 50, the door member is preferably only moved to the open position to permit cleaning of other internal mechanisms disposed within the cutting head, whenever needed.

With reference to FIG. 5, the cutting element 70 will now be discussed. First, in the preferred embodiment, the cutting element 70 is disposed within the main housing 51 at about 20 to 30 degrees from the horizontal plane. Further, the cutting element 70 preferably includes a blade having a sharpened cutting edge 71, the cutting tip of which is preferably formed to have an angle of approximately and generally between 5 to 10 degrees from the horizontal axis of the blade. To accomplish these preferred goals, in a preferred embodiment, the cutting element 70 comprises a cutting blade operably connected to a blade holder 72. The blade holder is in turn, operably connected and disposed within the interior chamber 88 of the cutting head assembly 50 in communication with the drive means 80, see FIG. 9, which are in turn operably coupled to the housing 51 of the cutting head assembly 50, and microkeratome generally. As has been described, the drive means 80 impart an oscillating movement to the blade holder 72, thereby causing the blade holder 72 and blade 71 connected thereto, to move back and forth within the interior chamber 88 of the cutting head assembly 50 and generally between opposite walls of the surrounding sidewall structure 53 thereof. Accordingly, the interior chamber 88 within housing 51 will be sized to receive both the cutting element, such as a cutting blade 70 and blade holder 72, and to permit the oscillating cutting movement of same within housing 51. So as to offer an improved microkeratome and cutting blade assembly that is able to cut and raise a microscopicly thin layer of corneal tissue in a manner that results in very fine, smooth and almost undetectable cut corneal tissue edges, in a preferred embodiment, the drive means 80 will cause the blade holder 72 and blade 71 to oscillate at a very rapid rate, higher than that accomplished by other devices, such as generally about 5,000 to 10,000 times per minute, and ideally about 8,500 times per minute so as to offer an optimal corneal cut. Further in this regard, and as explained further below, the drive means will preferably drive the cutting head assembly 50 across the positioning ring 30 and eye held therein, at a speed which takes the cutting head assembly 50 generally between 3 to 6 seconds, and ideally about 4 or 5 seconds. These preferred ranges for the cutting speeds of the microkeratome are thought to offer optimal and markedly improved cutting of the corneal tissues.

In addition, in order to accomplish the desirable goal of easily and quickly installing the cutting element 70 within the cutting head assembly 50, without excessive handling so as to maintain sterilization, the present invention comprises a cutting blade assembly, illustrated in FIGS. 6–8 and generally indicated by reference numeral 300. The cutting blade assembly 300 of the present invention is seen to comprise an improved cutting blade 310 and blade holder 320. The cutting blade 310 comprises a front portion 312 that includes a sharp, forward cutting edge 313, a rear, trailing portion 314 having a rear edge, 315, and a pair of side edges, 316, 317 that extend and taper between the front and rear trailing portions. In a preferred embodiment, the rear edge 315 is generally parallel to the forward cutting edge 313 of front portion 312. Also, the cutting blade 310 further includes at least one aperture, 318 formed therein, and preferably, a pair of apertures, 318 and 319 which are ideally circular in shape and disposed in the rear, trailing portion 314 in general alignment with one another. Preferably, the cutting blade 310 is substantially flat and made of stainless steel, with the front portion 312 of the cutting blade having an overall dimension which is larger than the rear trailing portion 314. In one embodiment, shown in FIG. 7, the side edges 316, 317 of the improved cutting blade 310' which extend between the front portion 312 and rear trailing portion 314, are rounded. This feature readily permits the operation of the cutting assembly 300 within the preferred microkeratome device that moves along an arcuate path over the position ring 32. More specifically, the cutting blade 310' shown in FIG. 7 is structured so that when it is oscillating during a surgery, wherein all or part of the blades' side edges might momentarily extend beyond the surrounding sidewall structure 53 of the cutting head assembly 50, it will not contact the positioning ring 32 nor otherwise interfere with the movement of the cutting head assembly 50 thereacross, along an arcuate path. The cutting blade 310, 310' can be formed to have other shapes to accomplish this same goal. For example, and as illustrated in FIGS. 6-A to 6-C, in a more preferred embodiment, the front portion 312 of the cutting blade 310 has a generally rectangular shape and the rear trailing portion 314 has a generally trapezoidal shape, such that the side edges 316, 317 thereof taper from a wider dimension of the front portion 312 to a smaller dimension in the rear trailing portion 314.

The cutting blade assembly 300 further comprises an improved blade holder 320. Blade holder 320 is formed so that an underside 321 thereof is secured to the cutting blade 310 at the at least one aperture 318 on the cutting blade, and so that a top side, 322, of the blade holder 320 includes means 325 for being operably driven by the drive means 80 of the microkeratome device. In the preferred embodiment, means 325 comprise a recess 326 formed within the blade holder, ideally having an oval shape, although the blade holder 320 could be formed to include a slot, groove or other shaped recess without departing from the scope of the present invention. Also in the preferred embodiment, the blade holder 320 will be molded of a plastic material and will be press fit during manufacture into the at least one aperture 118 on the cutting blade 310 so as to provide an integrally formed cutting blade assembly. It should be pointed out that by integrally forming the cutting blade 310 and blade holder 320, both parts which are contaminated during surgery, the cutting blade assembly 300 can be more readily removed from the cutting head 50 of the microkeratome, and further, if the blade holder 320 is formed of plastic, the cutting blade assembly 305 can be readily disposed of. Preferably, the blade holder 320 includes at least one lock segment 328 on its undersurface 321, which is structured and disposed to extend through the aperture 318 formed in the cutting blade 310 so as to become secured thereto. Most preferably, the blade holder includes a pair of lock segments formed to be circular in shape and which are structured to be snugly received within the preferred pair of apertures 318, 319 formed on the blade 310. Also in the preferred embodiment, the lock segment 328 includes a flanged portion 329 which is structured to engage at least partially about an edge of the aperture formed within the blade 310.

Referring now to FIG. 8, in a most preferred embodiment, the cutting blade assembly 300 of the present invention is seen to additionally comprise a tool 330 which facilitates the removal of the cutting blade 310 and blade holder 320 from a sterile packing container and the insertion thereof in a microkeratome device, while maintaining sterility. Preferably this tool is in the form of a handle assembly 360 connected to the blade holder 320 and structured to facilitate the introduction of the cutting blade assembly 300 into the access opening 156 of the cutting head assembly 50. In the preferred embodiment, the handle assembly 360 includes an elongate stem 362 structured to be threadingly coupled to the blade holder, ideally along a side wall thereof, so as to facilitate the introduction and installation of the cutting blade assembly 300 to and within the cutting head assembly 50. If desired, in this embodiment or in other embodiments, the handle assembly can be structured to permit the elongate stem 362 to be reconnected with the blade holder so as to remove a contaminated cutting blade assembly from the cutting head assembly 50, following a surgery. In an alternative preferred embodiment, the handle assembly 360 may include an elongate stem integrally formed with the blade holder and structured to be separated therefrom upon introduction and installation of the cutting blade assembly within the cutting head assembly 50. It should be appreciated that in this alternative preferred embodiment, the handle assembly may be comprised of a suitable plastic material so that it can be integrally formed with the preferred blade holder 320, and the entire cutting blade assembly can then be readily packaged in containers that permit sterilization prior to shipping, and which remain sterilized during shipping. In this way, the handle assembly 360 with the cutting blade assembly 300 connected thereto, can be easily removed from the sterile packaging and the handle assembly 360 used to quickly and easily insert the cutting blade assembly 300, while maintaining it in a sanitary condition, into the microkeratome's cutting head assembly, 50. Thereupon, the handle assembly 360 can be broken off from the cutting blade assembly 300 and discarded or otherwise disposed of.

Referring back now to FIG. 5, other features of the preferred microkeratome device will be described. In the preferred embodiment, the housing 51 of cutting head assembly 50 will include depth adjusting means 75 for adjusting the depth at which cutting element 70 cuts into the cornea. As illustrated in FIG. 5, the depth adjusting means 75 are preferably disposed at the front end face 52 of main housing 51 and form at least a portion of the bottom wall of housing 51 near front end face 52. Preferably, the depth adjusting means 75 comprise a separate nose segment 76, which is structured to be securely, yet removably interconnected with housing 51 by way of a conventionally known fasteners 74 such as a screw, a bolt, etc. Preferably, the nose segment 76 comprises an engagement segment 77 and a variable depth plate member 78. Engagement segment 77 preferably includes a terminal end 79 which is formed to define an inverted "V" shape, and preferably extends across the width of the nose segment 76. This structure is sized and configured to be received and to nest within a corresponding void, also shaped like an inverted "V", formed within housing 51 on and between oppositely disposed sidewall structures 53, adjacent front end face 52. It will be appreciated that this structure permits a highly stable nesting or dwelling of terminal end 79 within housing 51 even as the cutting head assembly 50 is moved along an arcuate path over positioning ring 32. Further, as illustrated, variable depth plate member 78 is preferably integral with engagement segment 77 and is disposed substantially in the horizontal plane. Variable depth plate member 78, has a depth depicted as "H" in FIG. 5, which is a dimension pre-selected by the surgeon to correspond the desired depth of the cut to be made into the cornea. Another feature of the present invention is to provide a plurality of nose segments 76, each including a plate member 78 having a differently dimensioned depth "H". It will be appreciated from FIG. 5 that there is an inverse relationship between the depth of plate member 78 and the depth of the cut to the cornea as the cutting head assembly 50 proceeds forward during surgery in the direction of the arrow "A" and pushes down on the cornea. For example, a plate member 78 having a larger depth "H" will shield more of the blade's cutting edge 71 whereas a plate member 78 having a smaller depth "H" will expose more of the area above the blade's cutting edge. It will thus be recognized that the cutting head assembly 50 is designed to be interchangeable with differently sized depth adjusting means 75 so as to precisely meet the needs of the patient undergoing surgery. Ideally, the present invention will offer two differently sized nose segments 76, namely one sized for 130 microns and another for 160 microns which are currently the most desirable depths for cutting into the cornea and exposing same for reshaping.

As has been described, housing 51 of cutting head assembly 50 also includes tracking means 60. Referring to FIG. 2, tracking means 60, which in the preferred embodiment are disposed on a lower peripheral zone of housing 51, are structured for mating communication with and tracking within channel member 42, see FIG. 3, of positioning ring 32. For example, in the preferred embodiment the tracking means 60 are disposed on the depth adjusting means 75 and are integral with and planar to the variable depth plate member 78 in the form of a flange 62, see FIG. 2. Preferably, flange 62 extends out beyond the periphery defined by surrounding sidewall 53 of housing 51 in generally perpendicular relation thereto. Further, although the cutting head assembly 50 is designed to receive nose segments 76 having variable depth plate members 78, flange 62 which extends therefrom is of a uniform height so as to correspond and effect mating communication with and tracking within channel member 42, of positioning ring 32. Although flange 62 could extend only from one side of the housing 51, in the preferred embodiment, flange 62 is disposed on each side of variable depth plate member 78, thereby facilitating use of the present invention on either a patient's left or right eye.

Also as previously recited, the main housing 51 includes abutting or stop means 65 which serve the purpose of limiting and preferably stopping, the forward movement of cutting head assembly 50 across positioning ring 32. In the preferred embodiment, stop means 65 are formed generally at rear end face 54 on surrounding sidewall structure 53 and are seen to comprise a shoulder 66 formed at the juncture between sidewall structure 53 and rear end face 54 of the housing 51, which shoulder is sized to be too large to pass within the channel member 42 of the guide means 40, thereby preventing any further forward motion of the head assembly 50 across positioning ring 32. When abutting engagement occurs between shoulder 66 and channel member 42, by way of lip 43', the driving means 80 can be stopped and then reversed to permit movement of the cutting head assembly 50 in the opposite direction. As has been described, it has been determined in recent years that in performing surgery on the cornea, the layers of the cornea which are cut should not be completely severed. A unique feature of the cutting head assembly 50 and of this invention 10 is that the cutting of the cornea, C, results in the formation of a corneal flap F, as illustrated in FIG. 1, which is also safely preserved by the assembly 50. To preserve the corneal flap F, housing 51 includes a flap receiving gap 59 formed within housing 51. As illustrated in FIG. 2 and more clearly in FIG. 5, flap receiving gap 59 is disposed generally near the front end face 52 of housing 51 and more particularly, is defined by a gap formed just forward of the blade's cutting edge 71 and just rearward of variable depth plate member 78. Thus, flap receiving gap 59 is disposed on an undersurface of housing 51 and extends upwardly and into housing 51. Ideally, flap receiving gap 59 extends through the opposite sidewall structure 53 of housing 51.

In preparation for cutting the cornea with the preferred microkeratome device: a) a sterilized improved cutting blade assembly 300 is slidably moved into position within the cutting head assembly 50, and b) the coupling member 90 is mounted on the cutting head assembly 50 and the drive means 80 connected to and engaged therewith. Referring to FIG. 2, as an additional feature, the cutting head assembly 50 may include indicia 67 for indicating to a surgeon which eye the device is in position to cut. For example, it is preferred that indicia such as the letter "L" as an abbreviation for "Left" or "left eye" and the letter "R" as an abbreviation for "Right" or "right eye" be utilized, or their equivalents in words or abbreviations in a foreign language or symbols. This indicia will preferably appear on opposite sides of the surrounding side wall structure 53 of the main housing 51 of the cutting head assembly 50, in a location which will be selectively concealed by the coupling member 90. In particular, when operably coupled with the cutting head assembly 50 and disposed over so as to cut the right eye, the coupling member 90 extends down the left side of the main housing 51 of the cutting head assembly 50, leaving only the right side, and preferred "R" indicia positioned thereon, visible. Conversely, when assembled to cut the left eye, the coupling member 90 extends down the right side of the housing 51, leaving only the left side and the indicia positioned thereon readily visible. As such, it is seen that a further safety feature directed towards ensuring proper alignment of the device on a patient's eye is achieved.

To continue, once the positioning ring 32 has been centrated on the eye with a proper vacuum applied to temporarily attach it thereto, c) the tracking means 60 of the head assembly 50 can be matingly connected to the guide means 40 of positioning ring 32 in an initial or start position. Once power is supplied to the microkeratome device, the cutting head assembly 50 may move across the positioning ring 32 with cutting of the cornea C, taking place until the stop means 65 contact channel member 42 of the positioning ring 32, to limit and preferably, prevent any further forward motion of the assembly. It should also be clear that in this stopped position, the cutting element 70 has not moved completely across the cornea C, but rather has cut a portion of the cornea up until this point, creating a corneal flap which is left attached to the cornea as designated by the area marked "F" which is shown in the FIGS. 10-A and 10-B. Moreover, as illustrated in FIG. 5, the corneal flap created has been directed by the forward movement of the assembly, upwardly and into flap receiving gap 59 of housing 51 to be preserved and kept clear of cutting element 70. Once the assembly has been stopped as in FIG. 10-B, the drive means 80 can be reversed to permit movement of the cutting head assembly 50 in the opposite direction, which does not result in any further cutting of the cornea, but rather, in the safe removal of the corneal flap F out of flap receiving gap 59 of housing 51. Thus, when the cutting head assembly 50 returns through to a position analogous to that shown in FIG. 10-A, it can be disengaged from the retaining means 30. The corneal flap F can then be maneuvered so as to permit the cornea to be reshaped, preferably by way of a laser surgical procedure. Once the surgery has been completed, the corneal flap is returned to a covering relation over cornea.

Another unique feature of the present invention is not only that a corneal flap can be created, but significantly, that the air corneal flap is positioned in such a way that the blinking of the eye will not improperly position the corneal flap on the cornea following surgery. Referring again to FIGS. 10-A and 10-B, the preferred microkeratome device is schematically illustrated on both a patient's left and right eyes. As depicted in FIG. 10-A, reference points of the work environment can be equated with the position of some numerals on the face of a clock. Thus, in FIG. 10-A, it will be noted that with respect to the patient's left eye, the cutting head assembly 50 in the initial position is preferably disposed at a generally five o'clock position. With respect to the patient's right eye, the cutting head assembly 50 in the initial position is preferably disposed at a generally seven o'clock position. Turning now to FIG. 10-B, the cutting head assembly 50 is shown to have moved towards a position generally aligned with the twelve o'clock position, wherein the stop means 65 are in abutting engagement with channel member 42 of the positioning ring 32, such that any further forward motion of the assembly is prevented. It will thus be appreciated that regardless of whether the surgical procedure is being performed on a patient's left or right eye, the cutting head assembly 50 is preferably aligned generally with a twelve o'clock position. It will also be appreciated from FIG. 10-B that the resulting corneal flap F, remains attached to the cornea at an upper region thereof. As a result, following the surgical procedure to reshape the cornea, the orientation of the corneal flap will be in generally the same direction as the natural blinking action. That is, it is believed that the downward blinking motion of the patient will tend to stroke the corneal flap down and thereby assist with maintaining the corneal flap in proper re-position on the cornea so as to avoid the development of astigmatism.

Figure 9:
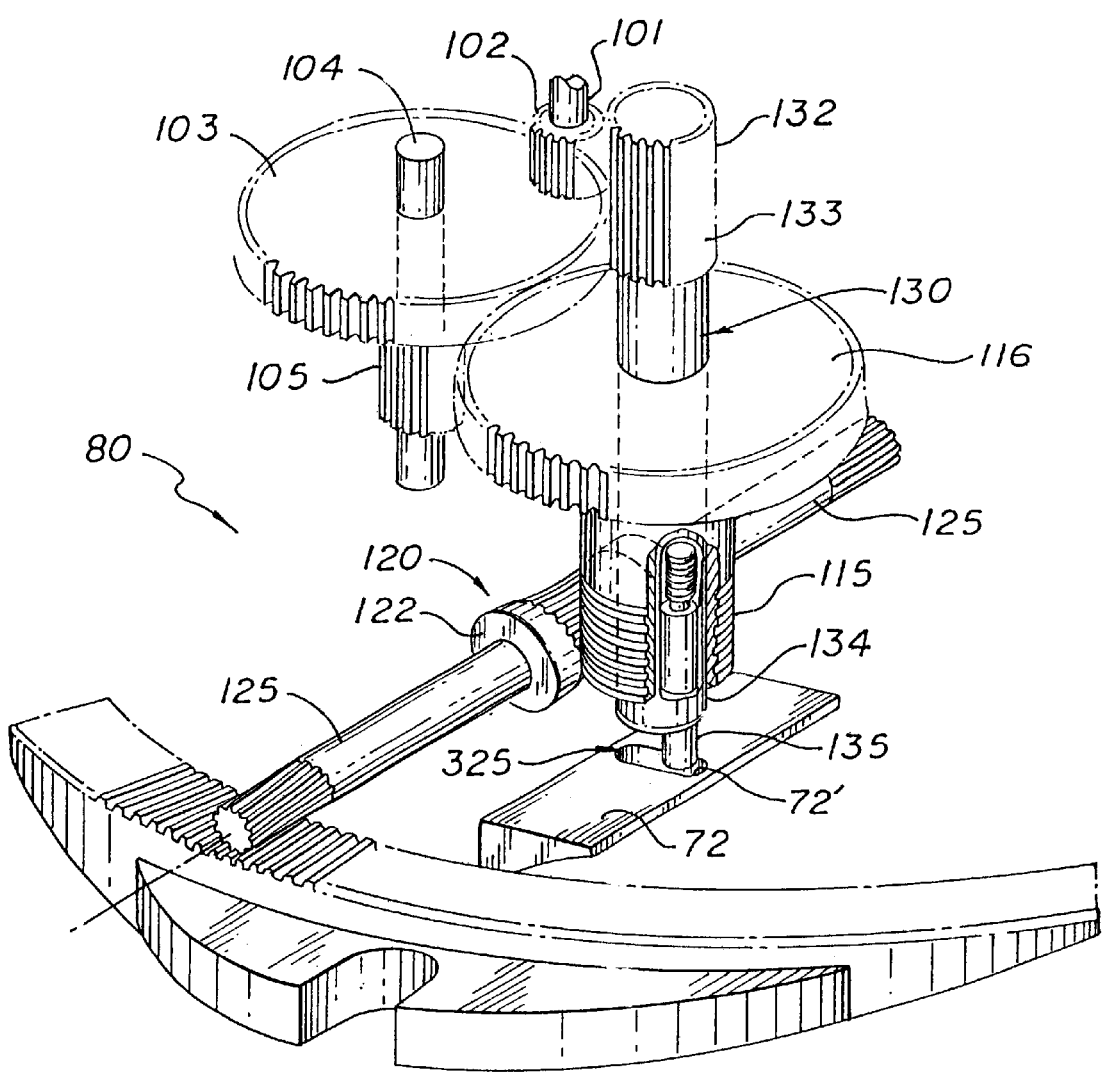
FIG. 9 is an isolated perspective view of the drive means for the preferred microkeratome device illustrating the operation and interconnection of the worm, worm gear, and oscillating shaft with the means of the blade holder, in the form of a recess, for being operably driven by the drive means of the microkeratome device.

Referring now to FIG. 9, the present invention includes drive means 80 both: a) for driving the cutting head assembly 50 across the previously described eyeball retaining and positioning means 30; and b) for causing the cutting element 70 to oscillate back and forth within housing 51. The drive means 80 in a most preferred embodiment will drive the cutting head assembly 50 across the eyeball retaining and positioning means 30 and eye held therein, at a speed which takes the cutting head assembly generally between 3 to 6 seconds in the first direction, and similarly in the opposite direction. Also, in a preferred embodiment, the drive means 80 include among other items, discussed below, a motor 100, which is electrically operated and more preferably, a micromotor capable of operating at a constant and uniform speed, regardless of the load. Specifically, under normal circumstances the natural resistance. encountered by the cutting head assembly 50, as it is driven over the cornea, would result in an increased torque load upon the micromotor, which would tend to cause a voltage drop in the internal resistance of the motor 100 and therefore a drop in speed. While some known systems for microkeratome devices attempt to avoid excessive drops in speed by incorporating an overpowered motor to keep losses below a 10% slow down, the motor 100 of the present invention is preferably equipped to monitor current flowing therethrough, such as by using an op amp, and to utilize that information to control the applied voltage and maintain a generally constant speed. This monitoring and compensation, sometimes referred to as I R compensation, thereby permits a conventional 12 V supply module, dropped through said compensation, to be used with a DC motor of lower nominal voltage, in order to maintain the effective constant speed of travel of the cutting head assembly 50 over the eye.

Figure 4:
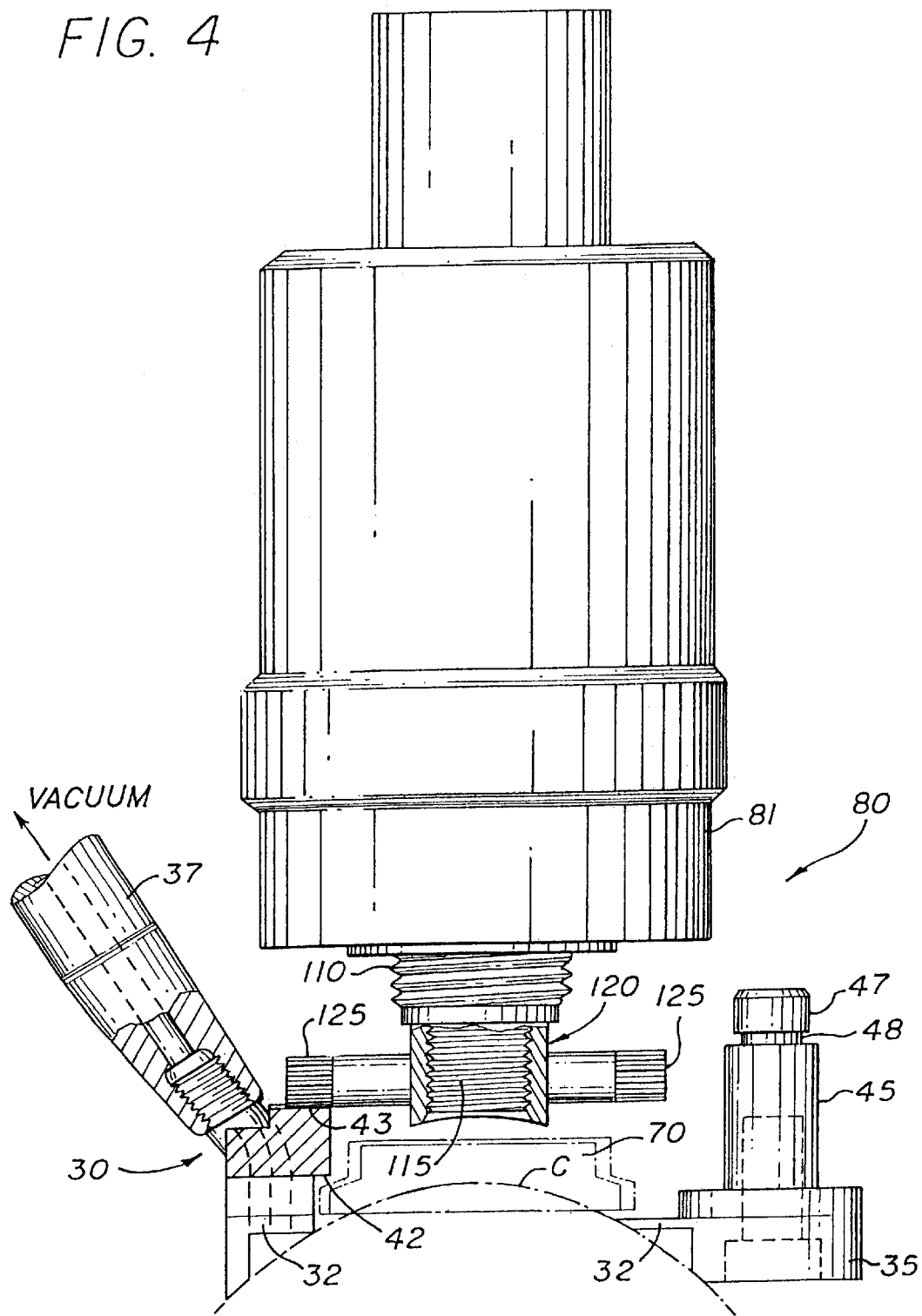
FIG. 4 is a partial side view of the preferred microkeratome illustrated in FIG. 2 in assembled form and in position on a patient's cornea.

Referring now to FIG. 4 and again to FIG. 9, the driving means 80 of the microkeratome device are seen in the preferred embodiment to further include a gear box 81 into which a motor main drive shaft 101 extends. From the gear box 81, and specifically concentrically through an engagement hub 110 as shown in FIGS. 4 and 5, a cutting assembly main drive shaft operatively extends. The cutting assembly main drive shaft comprises two primary sections, namely: a) a threaded drive screw or "worm" 115 shown in FIG. 9, which is an intermediate section that extends through the engagement hub 110; and b) an oscillation shaft 130, also shown in FIG. 9, and which is the inner most section and extends through the worm 115.

Turning first to the engagement hub 110, shown in FIG. 4, it is an outer most section that preferably extends downwardly from the gear box 81 and is structured to be matingly, and preferably threadingly engaged within the threaded aperture 58 formed in the main housing 51. As such, the engagement hub 110 functions to secure the drive means 80 to the cutting head assembly 50. Further, it will be recognized that the drive means 80 are thereby permitted to enter the cutting head assembly 50 through a top surface 56' and are thus, generally vertically disposed. It is believed that this feature results in less interference with the surgical field and facilitates finer handling by the surgeon than is offered by conventionally known microkeratomes. Specifically, known microkeratomes have typically provided for horizontally disposed drive means, which resulted in the surgeon having to handle a cord of the driving means, which if not held properly could cause drag on the operation of the microkeratome and/or result in a different pressure being applied to the microkeratome. Moreover, the structure of the present invention maintains its center of gravity substantially over the center of the eye, unlike old systems, thereby providing increased balance and ensuring that the cutting head assembly does not inadvertently tip away from the surface of the eye during use.

As illustrated in FIG. 5, the oscillation shaft also extends from the gear box 81. Turning now to FIG. 9, the oscillation shaft 130, which extends into the housing 51 through its aperture 58, is preferably an independent element that extends concentrically through and protrudes from both ends of the worm 115. The oscillation shaft 130, which is preferably structured to freely rotate relative to the worm 115 includes an upper drive portion 132 which may be welded onto shaft 130 but which is in any event, drivingly engaged with a main drive gear 102 secured to the motor main drive shaft 101. Accordingly, rotation of the motor main drive shaft 101 results in corresponding rotation of the oscillation shaft 130. Further, protruding off center from an opposite end 134 of the oscillation shaft 130 is an oscillation pin 135. The oscillation pin 135, which is preferably downwardly biased to maintain engagement pressure on the cutting element 70 is structured to extend into a slot 72' formed in an upper surface of the preferred blade holder 72 or other means 325 formed on the blade holder for receiving the oscillating pin and permitting it to impart movement thereto. As such, upon axial rotation of the oscillation shaft 130, the oscillation pin 135 rotates a predetermined radius off center and alternatingly engages opposite side edges of the slot 72' of the blade holder 72 to result in alternating, oscillating movement of the blade holder 72 and the cutting blade held thereby.

Still referring to FIG. 9, the oscillating shaft 130 further includes a secondary drive portion 133. The secondary drive portion 133 is drivingly connected with a first interior drive gear 103 contained within the gear box 81. The first interior drive gear 103 is connected with and is drivingly secured to an interior drive shaft 104, which preferably includes a second interior drive gear 105 disposed thereon in spaced apart relation from the first interior drive gear 103. As such, upon rotation of the oscillation shaft 130, the second interior drive gear 105 also rotates.

Again with reference to FIG. 9, drivingly connected with the second interior drive gear 105 and structured to extend from an interior of the gear box 81, concentrically through the engagement hub 110, is the threaded drive screw or "worm" 115. The worm 115, which extends up into the gear box 81 includes a drive head 116 which engages the second interior drive gear 105. As a result, upon rotation of the interior drive shaft 104, the worm 115 correspondingly rotates within the housing 51 of the cutting head assembly 50. Further, rotatably disposed within the housing 51, in operative engagement with the worm 115, is a worm gear 120. The worm gear 120 preferably includes an increased diameter central portion 122 having a plurality of drive recesses formed about a perimeter thereof and structured to engage the exterior threaded surface of the worm 115 such that the central portion 122, and accordingly the entire worm gear 120, rotates about a horizontal axis as a result of the rotation of the worm 115 about a vertical axis. It is noted that the screw-like threaded surface of the worm 115 enables the worm 115 to rotate without moving vertically and successively engage the drive recesses on the worm gear 120 to effect rotation thereof. Extending from at least one, but preferably both vertical faces of the central portion 122 of the worm gear 120 is a propulsion shaft 125. The propulsion shaft 125, which comprises additional tracking means, is structured to protrude from the sidewall structure 53 of the main housing 51 and engage the toothed track 43 on the positioning ring 32 such that upon rotation of the worm gear 120, and accordingly rotation of the propulsion shaft 125, the propulsion shaft 125 rides along the toothed track 43 and drives the cutting head assembly 50 across the positioning ring 32 smoothly and at a steady and defined pace. Furthermore, it is seen that by reversing the rotational direction of the interior drive shaft 101 within the gear box 81, the direction of rotation of the worm 115 and therefore the worm gear 120 are reversed to effectuate reverse driven movement of the cutting head assembly 50 over the positioning head 32. Also, so as to facilitate movement over toothed track 43 and the arcuate path thereof, it is preferred that the propulsion shaft 125 portion of the worm gear 120 include a helical gear configuration or plurality of angled ridges to permit more effective alignment with the curved toothed track 43 and movement thereover.

Considering the motor 100, once again, it is preferred that it be controlled by a foot pedal or like actuation means. In the case of a foot pedal, it is preferred that it be a dual function foot pedal such that one side will function to drive the motor main drive gear 101, and therefore the cutting head assembly 50 in a forward direction, and the second side will drive them in a reverse direction. Further, the system may be set to a manual mode whereby a doctor must affirmatively reverse the direction of movement, or an "auto-reverse" mode wherein upon the cutting head assembly 50 traveling its maximum distance it automatically reverses direction. In either case, however, the device will preferably be equipped with a sensor, such as a proximity sensor of any type or as in the preferred embodiment a sensor associated with the motor 100 and structured to detect an abrupt current increase such as that exhibited upon encountering a mechanical stop. Specifically, when the cutting head assembly 50 reaches the stop means 65 and further forward movement is either partially or completely resisted, an abrupt current increase will generally occur in the motor 100. That abrupt current increase, once detected, can signal either the power to shut off, or the reverse movement to commence, depending upon a doctor's desired setting.

As has been described, the preferred microkeratome device can be utilized on both eyes of the patient, see FIG. 10-A and 10-B. Specifically, as worm gear 120 runs through housing 51 and juts out of the opposite surrounding sidewall structure 53 of housing 51, the cutting head assembly is ready to use on the opposite eye of a patient. In order to accomplish this, and due to the symmetric shape of the cutting head assembly 50, the drive means 80 need only be removed from the housing 51 and thus, coupling member 90, whereupon, it can be re-oriented 180 degrees for use with the opposite eye of a patient.

Considering the drive means 80 once again, it should be noted that they must generally operate in conjunction and in harmony with the suctioning means applied to the positioning ring 32 when surgery is performed on an eye. Accordingly, the present invention is further directed towards incorporating both the drive means 80 and the suctioning means as part of an overall control assembly 200. The control assembly 200 of the present invention includes a portable housing 205 from which power and control are supplied through a cable 203 to the portion of the drive means 80 which interact with the cutting head assembly 50, and from which a vacuum source of the suctioning means is supplied through the vacuum hose 202. The suctioning means and the vacuum source which it provides will be addressed first. Specifically, the vacuum source generally includes a vacuum pump 210 contained within the housing 205, which is powered from a conventional power supply, such as an internal or external power module and/or power source, and which operates to create the vacuum which results in a suction at the positioning ring. In addition to the vacuum pump 210, however, the suctioning means of the present invention further include a reserve vacuum tank 215. The reserve vacuum tank 215 is structured to be evacuated upon activating the control assembly 200 and maintained generally at an operational level. Moreover, in the event that the operation of the vacuum pump is interrupted, such as due to a power loss, the reserve vacuum tank 215 is preferably structured to maintain a sufficient vacuum to continue the positioning ring's hold on the eye until the movement of the cutting head assembly 50 over the eye is completed. Specifically, the control assembly 200 is structured such that the reserve vacuum tank 215 is preferably continually operational and such that in the event of a power loss or other interruption to the operation of the vacuum pump 210, a check valve isolates the vacuum pump 210, the necessary vacuum is maintained by the reserve vacuum tank 215, and a complete cutting pass across the eye is not dangerously and unexpectedly interrupted due to an interruption in the operation of the vacuum pump 210.

According to the present invention, the vacuum pump 210 is preferably controlled by a computerized processor control 220 within the housing 205. The processor control 220 performs a number of functions at all times including when the control assembly 200 is turned on and/or is in a "Ready" mode. In particular, when the control assembly 200 is first turned on, it is structured to conduct a number of internal tests, as indicated on a display screen 211, and the vacuum pump 210 is preferably directed to first generate a vacuum in the reserve vacuum tank 215. Next, the vacuum pump 210 will preferably continue to run until a desired vacuum relative to atmospheric pressure is generated. Once the desired vacuum is achieved, however, operation of the vacuum pump is cycled. For example, once a desired level is attained, the vacuum pump 210 is turned off until the vacuum drops below a certain point relative to atmospheric pressure. At that point, the vacuum pump 210 is preferably turned on once again by the processor control 220 in order to raise the vacuum back up above the desired level. In this manner, an operable back-up vacuum is available, if ever it should be needed.

In the preferred embodiment, the control assembly 200 remains in the "Ready" mode until a user wishes to begin an operation or to conduct further testing, if that is desired. When, however, it is time to begin an operation, a user typically presses a foot pedal 216 or other switch to activate the vacuum and shift the control assembly into an "Operating" mode. Before entering the "Operating" mode, a "Pre-op" mode is preferably initiated wherein the control assembly 200 completes a number of internal tests. Unlike the "Ready" mode, once in the "Operating" mode, the vacuum pump 210 will preferably remain on, thereby ensuring that a sufficient vacuum will always be present. Furthermore, so as to ensure that a malfunction in the processor control 220 does not interrupt the cutting process, once the "Operating" mode is entered, control of the motor 100, to be described in greater detail subsequently, is preferably removed/interrupted from the processor control 220, such that the processor control 220 only acts in an advisory capacity as to the performance of the motor 100 and mechanism, providing warning messages and data, and is transferred to an independent logic control 225, such as one embodied in one or more PAL chips. Preferably, this transfer of control is achieved utilizing at least one latching switch 228 connected between the processor control 220 and the independent logic control 225. The latching switch 228 is normally positioned so that the processor control 220 at least partially directs the operation of the motor 100, however, when the "Operation" mode is entered, it is switched so as to eliminate dependency on the processor control 220, so that the back up power source 260 becomes operational, and so that the independent logic control 220 directs the operation of the motor 100 without processor influence. Preferably, this "Operation" mode orientation of the latching switch 228 is maintained until affirmatively reset by a user. For example, pressing foot pedal 216 once again will reset control to its "Ready" mode state.

Still addressing the suctioning means, although the powering of the vacuum pump 210 may require a high voltage, it, as well as all other high voltage aspects of the control assembly 200, must be isolated from a low voltage portion of the circuity which comes into contact with the patient. In this regard, in some instances a momentary removal of power to the vacuum pump 215 can sometimes occur, thereby requiring a resetting of certain conditions before the pump can restart and normal running can proceed. For example, in the preferred embodiment, if while in the "Operate" mode the current drawn by the vacuum pump 215 momentarily jumps from approximately 0.6 amps to approximately 1.3 amps, the control assembly 200 will generally identify a pump restart. If the pump fails to restart, the vacuum reserve tank operates to maintain the vacuum so as to enable a surgery in progress to be completed. Normally, however, the pump is able to restart, and normal running of the vacuum pump resumes. However, even if the vacuum pump is able to restart, the vacuum pump will typically not resume operation if a full vacuum is still present, thereby requiring a momentary release of vacuum prior to achieving the restart. The release of vacuum, however, is triggered from controls on the low voltage side of the control assembly 200. Therefore, the present invention preferably utilizes an optic switching assembly 240 to trigger the momentary release of vacuum with the required electrical isolation. In particular, when the previously described typical current jump associated with a pump restart is exhibited, that current jump typically gives rise to an instantaneous voltage increase from a normal peak of less than 0.9 v to a normal peak of at least 1.25 v across a preferably 0.75 ohm resistor 241, and is sufficient to illuminate an LED 242 of an optic coupler 240'. The LED 242 illuminates a light actuated semi conductor 243 of the optic coupler 240' via a galvanically isolated path. Preferably through a pulse extender, a semi-conductor chip 245 is then actuated and in turn actuates a valve 247 to cause the momentary release in vacuum required for the restart and continuing operation of the vacuum pump 210. Accordingly, complete isolation is maintained between the high voltage and low voltage sides of the assembly. Indeed, this process is also utilized during the described pump cycling in the "Ready" mode.

Turning now to the other aspect affected by the control assembly 200, namely, the drive means 80, they are preferably powered by a motor 100, such as low power DC, pneumatic or hydraulic motor. The motor 100 is sufficient to drive the cutting head assembly 50 across a positioning ring, such as 32, and will preferably operate in both a forward and a reverse direction. Furthermore, during normal forward operation, the control assembly 200 is structured to detect an increase in amperage above a certain shut off limit that has been predetermined by the user or manufacturer according to the operating environment and the type of microkeratome device with which the control assembly 200 is being used. The shut off limit is typically a 300 milliamp level, which is a typical indication that movement of the cutting head assembly 50 has been blocked and that the activity of the motor 100 and drive means is being resisted. A stop of the cutting head assembly 50 can occur either due to the presence of an obstacle on the cutting path over the positioning ring, such as a number of eyelashes or other debris, or due to the normal stopping of the cutting head assembly 50 because it has made a complete cut reaching the mechanical stop means. In any event, however, if the motor 100 pulls to the 300 milliamp level after a normal 3 second run, the motor 100 shuts off and is dynamically braked until restarted by the user. Specifically, when dynamically braking the motor, the control assembly 200, whether it is used with the positioning ring and cutting head assembly of the preferred microkeratome device disclosed herein or another known or to be developed microkeratome device, preferably affirmatively resists advancement bf the motor through a strong retarding force. To restart, in preferably only an emergency situation, the user may temporarily remove pressure from the foot pedal 252 so as to restart and then again activate the foot pedal to result in a continued movement of the motor 100 for another three (3) seconds, during which the only limitation upon the power to the motor 100 is a defined current limit of preferably approximately 400 milliamps. Indeed, this more absolute limit of 400 milliamps is in effect at all times, including during motion in both the forward and reverse directions.

In addition to stopping the operation of the drive means 80 because of a movement stoppage, in the event of a loss of suction at the positioning ring, which may result in temporary or complete detachment of the positioning ring from the eye, the control assembly 200 is preferably further structured to immediately shut off and dynamically brake the motor 100, and therefore, the drive means. As a result, the cutting head assembly 50 will not continue to cut if there is even a momentary break in the suction of the positioning ring to the eye. Moreover, if such a shut down occurs, complete re-initiation of the operating mode, including the normal array of systems checks and the re-establishment of the vacuum, must preferably be achieved before operation of the motor 100 can resume. Still, re-initiation is never recommended until after a proper healing period has passed.

As indicated, the vacuum pump 210 of the present invention preferably includes a backup, in the form of the vacuum reserve tank 215, that maintains vacuum if the vacuum pump 210 fails, such as due to a power loss. Similarly, the motor 100 preferably includes a backup power source 260, such as one or more lithium batteries, disposed within the housing 205 of the control assembly 200. The backup power source 260 is most preferably included within and as part of the control assembly 200 and functions to immediately continue to supply operating power to the motor 100 in case of a power loss from a typical power supply, whether an internal module and/or external source. As such, a completed pass across the eye can be normally completed if a power failure occurs.

Lastly, it is noted that in some instances a user that is monitoring patient conditions may already be viewing a computer display console that monitors other patient conditions. As such, the control assembly 200 of the present invention includes a connection port 265, such as a serial connection port, through which a computer interface can be achieved and through which data relating to the operation of the control assembly 200 can be transmitted for convenient use and display on the computer display console. An electrically isolated, bi-directional computer port, such as an RS232 port with optically isolated data and transformer isolated power is preferred for communication with a host laser system or isolated computer system. For example, the laser systems typically employed in the corrective procedures generally include an elaborate computer control. This laser computer control directs the corrective procedure and monitors the status of the operation throughout. As such, by interfacing the control assembly 200 with the laser computer control, the actual operating conditions of the present invention can be equivalently monitored and recorded.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A surgical device for cutting substantially across a cornea of an eye of a patient, said device comprising:
   a) a positioning ring structured to be temporarily attached to a portion of the eye surrounding the cornea to be cut;
   b) a suctioning assembly structured to at least temporarily attach said positioning ring to the portion of the eye surrounding the cornea;
   c) a cutting head assembly including a cutting element positioned therein for cutting the cornea;
   d) a drive assembly operably connected to said cutting head assembly for causing movement of said cutting element; and
   e) a control assembly, said control assembly including a processor control structured to regulate a functioning of said drive assembly, said processor control being interrupted and an independent logic control being activated to regulate said functioning of said drive assembly upon an initiation of operation of said suctioning assembly.

2. A surgical device as recited in claim 1 wherein said drive assembly is structured to cause oscillating movement of said cutting element.

3. A surgical device as recited in claim 1 wherein said drive assembly is structured to cause movement of said cutting element by causing movement of said cutting head assembly across the eye of the patient.

4. A surgical device for cutting substantially across a cornea of an eye of a patient, said device comprising:
   a) a positioning ring structured to be temporarily attached to a portion of the eye surrounding the cornea to be cut;
   b) a suctioning assembly structured to temporarily attach said positioning ring to the portion of the eye surrounding the cornea;
   c) a cutting head assembly including a cutting element positioned therein for cutting the cornea;
   d) a drive assembly operably connected to said cutting head assembly for causing movement of said cutting element;

e) a control assembly, said control assembly including at least said drive assembly; and f) said drive assembly of said control assembly being structured to dynamically brake upon detection of an increase in amperage above a shut off limit.

5. A surgical device as recited in claim 4 wherein said drive assembly is structured to cause oscillating movement of said cutting element.

6. A surgical device as recited in claim 4 wherein said drive assembly is structured to cause movement of said cutting element by causing movement of said cutting head assembly across the eye of the patient.

7. A surgical device for cutting substantially across a cornea of an eye of a patient, said device comprising:

a) a positioning ring structured to be temporarily attached to a portion of the eye surrounding the cornea to be b) a suctioning assembly structured to temporarily attach said positioning ring to the portion of the eye surrounding the cornea;

c) a cutting head assembly including a cutting element positioned therein for cutting the cornea;

d) a drive assembly operably connected to said cutting head assembly for causing movement of said cutting element;

e) a control assembly, said control assembly including at least said drive assembly and said suctioning assembly;

f) said drive assembly including a motor, said motor being connected to a power supply; and g) a backup power source structured to immediately supply power to said motor upon an interruption of power being supplied by said power supply.

8. A surgical device as recited in claim 7 wherein said drive assembly is structured to cause oscillating movement of said cutting element.

9. A surgical device as recited in claim 7 wherein said drive assembly is structured to cause movement of said cutting element by causing movement of said cutting head assembly across the eye of the patient.

* * * * *